United States Patent [19]

Hannam et al.

[11] Patent Number: 5,649,959
[45] Date of Patent: Jul. 22, 1997

[54] ASSEMBLY FOR SEALING A PUNCTURE IN A VESSEL

[75] Inventors: Peter Henry Hannam, Worthing, United Kingdom; Richard Dale Allison, Woodinville, Wash.

[73] Assignee: Sherwood Medical Company, St. Louis, Mo.

[21] Appl. No.: 389,839

[22] Filed: Feb. 10, 1995

[51] Int. Cl.⁶ ................................................ A61B 17/00
[52] U.S. Cl. .......................... 606/213; 606/214; 604/43; 604/93; 604/181; 604/257
[58] Field of Search ............................. 606/213, 214, 606/1; 604/164, 170, 181, 257, 275, 39, 43, 40, 36, 92, 81, 93

[56] References Cited

U.S. PATENT DOCUMENTS

| | | |
|---|---|---|
| 581,235 | 4/1897 | Kenyon . |
| 1,191,736 | 7/1916 | Roberson . |
| 1,794,221 | 2/1931 | Washburn et al. . |
| 2,898,913 | 8/1959 | Ritter et al. . |
| 3,016,895 | 1/1962 | Sein . |
| 3,056,408 | 10/1962 | Brown . |
| 3,447,533 | 6/1969 | Spicer . |
| 3,516,403 | 6/1970 | Cournut . |
| 3,572,335 | 3/1971 | Robinson . |
| 3,587,586 | 6/1971 | Kronenthal . |
| 3,675,639 | 7/1972 | Cimber . |
| 3,804,097 | 4/1974 | Rudie .................... 604/51 |
| 3,874,388 | 4/1975 | King et al. . |
| 4,007,743 | 2/1977 | Blake . |
| 4,154,226 | 5/1979 | Hennig et al. . |
| 4,182,339 | 1/1980 | Hardy, Jr. . |
| 4,364,392 | 12/1982 | Strother et al. . |
| 4,390,018 | 6/1983 | Zukowski . |
| 4,453,930 | 6/1984 | Child .................... 604/59 |
| 4,577,631 | 3/1986 | Kreamer . |
| 4,578,061 | 3/1986 | Lemelson ............. 604/164 |
| 4,587,969 | 5/1986 | Gillis . |
| 4,588,395 | 5/1986 | Lemelson ............. 604/59 |
| 4,606,337 | 8/1986 | Zimmermann et al. . |
| 4,610,248 | 9/1986 | Rosenberg . |
| 4,619,261 | 10/1986 | Guerriero . |
| 4,638,803 | 1/1987 | Rand . |
| 4,645,488 | 2/1987 | Matukas ............... 604/59 |
| 4,669,474 | 6/1987 | Barrows . |
| 4,708,718 | 11/1987 | Daniels ................ 604/53 |
| 4,710,192 | 12/1987 | Liotta et al. .......... 623/1 |
| 4,744,364 | 5/1988 | Kensey . |
| 4,749,689 | 6/1988 | Miyata et al. ......... 514/21 |
| 4,774,091 | 9/1988 | Yamahira et al. ..... 424/426 |
| 4,790,819 | 12/1988 | Li et al. ............... 604/59 |
| 4,829,994 | 5/1989 | Kurth . |
| 4,832,688 | 5/1989 | Sagae et al. .......... 604/53 |
| 4,838,280 | 6/1989 | Haaga . |
| 4,850,960 | 7/1989 | Grayzel ............... 604/158 |
| 4,852,568 | 8/1989 | Kensey . |
| 4,871,094 | 10/1989 | Gall et al. ............ 222/386 |
| 4,878,906 | 11/1989 | Lindemann et al. ... 623/1 |
| 4,890,612 | 1/1990 | Kensey ................ 606/213 |
| 4,895,564 | 1/1990 | Farrel ................. 604/164 |

(List continued on next page.)

FOREIGN PATENT DOCUMENTS

| | | |
|---|---|---|
| 0482350 | 4/1992 | European Pat. Off. . |
| 0493810 | 7/1992 | European Pat. Off. . |
| 1509023 | 4/1978 | United Kingdom . |
| 1569660 | 6/1980 | United Kingdom ..... 604/57 |
| 9014796 | 12/1990 | WIPO . |
| 9109641 | 7/1991 | WIPO ................... 604/49 |
| 9205740 | 4/1992 | WIPO . |

*Primary Examiner*—Jeffrey A. Schmidt
*Attorney, Agent, or Firm*—Montgomery W. Smith; Richard D. Allison

[57] ABSTRACT

A bioabsorbable assembly for sealing an incision or puncture in the body of the patient including a first member which is positioned generally along the wall of the blood vessel, duct, body cavity or lumen of the patient and a gelatinous material which is injected into the incision or puncture around a filament or clip member which is associated with the first member to seal the incision or puncture from the flow of fluids through the blood vessel, duct or lumen of the patient and the method therefore.

28 Claims, 14 Drawing Sheets

U.S. PATENT DOCUMENTS

| | | | |
|---|---|---|---|
| 4,900,303 | 2/1990 | Lemelson | 604/54 |
| 4,929,246 | 5/1990 | Sinofsky | 606/8 |
| 4,941,874 | 7/1990 | Sandow et al. | 604/60 |
| 4,950,234 | 8/1990 | Fujioka et al. | 604/60 |
| 4,994,028 | 2/1991 | Leonard et al. | 604/60 |
| 5,021,059 | 6/1991 | Kensey et al. | 606/213 |
| 5,041,090 | 8/1991 | Scheglov et al. | 606/195 |
| 5,053,046 | 10/1991 | Janese | 606/215 |
| 5,061,274 | 10/1991 | Kensey | 606/213 |
| 5,108,407 | 4/1992 | Geremia et al. | 606/1 |
| 5,108,421 | 4/1992 | Fowler | 606/213 |
| 5,129,882 | 7/1992 | Weldon et al. | 604/53 |
| 5,383,899 | 1/1995 | Hammerslag | 606/214 |
| 5,391,183 | 2/1995 | Janzen et al. | 606/213 |
| 5,403,278 | 4/1995 | Ernst et al. | 604/60 |
| 5,413,571 | 5/1995 | Katsaros et al. | 606/213 |
| 5,443,481 | 8/1995 | Lee | 606/213 |

ASSEMBLY FOR SEALING A PUNCTURE IN A VESSEL

BACKGROUND OF THE INVENTION

This invention relates generally to medical devices and more particularly to hemostatic devices for the closure of various openings or incisions in the body of a patient.

As will be appreciated by those skilled in the art, various surgical procedures are now being carried out intravascularly or intraluminally. For example, in the treatment of vascular disease, such as atherosclerosis, it is common practice to invade the artery to insert an instrument or catheter, e.g., a balloon or other type of catheter to carry out the procedure within the artery. Such procedures usually involve the percutaneous puncture of the artery so that an introducer sheath can be inserted into the artery and thereafter the instrument or catheter itself can be inserted through the sheath to the operative position within the artery. One problem with this type of procedure is that it is oftentimes difficult to stop the bleeding at the percutaneous puncture after the procedure has been completed and after the instrument (and any introducer sheaths used therewith) have been removed.

At present, the most common treatment to stop such bleeding is by the application of manual pressure over the puncture site by a trained physician or other suitably trained medical personnel. Such manual pressure has to be applied for a sufficiently long time for hemostasis to occur so that the opening is effectively closed against further bleeding. In the case of punctures into femoral or superficial femoral arteries, the pressure may have to be applied for forty-five minutes or more for hemostasis to occur. Not only is the application of manual pressure wasteful of time by highly skilled medical professionals, the procedure results in a substantial reduction, if not virtual arrest, of the flow of blood through the vessel. Since thrombosis is one of the major side effects that may occur in the immediate post operative period, any reduction in blood flow, such as caused by the application of manual pressure, is undesirable.

Simple applicator devices have been disclosed in the patent literature for inserting an absorbent plug or member into the vagina. Such devices basically comprise a tubular element adapted to be inserted into the vagina and having a plug of absorbent material located therein. The device also includes a plunger to push the plug out of the tubular element into the vagina. The plug may also include a thread or string attached to it to enable the plug to be retrieved from the vagina. Examples of such devices are shown in U.S. Pat. Nos. 1,191,736 granted to Robertson and 1,794,221 granted to Washburn et al.

While such devices are suitable for their intended purposes, there is no suggestion of their use, nor are they particularly suitable for insertion into an opening in the wall of a blood vessel or other bodily lumen or duct to seal that opening.

U.S. Pat. Nos. 4,744,364 and 4,852,568 granted to Kensey, disclose a positioning instrument and a closure or anchor device for sealing an opening in tissue which separates one portion of the body of a living being from another portion, e.g., a puncture in a blood vessel, duct or lumen, of a living being. Various methods of use for that device are also disclosed in these patents. The positioning instrument of the Kensey invention basically comprises an elongated tubular body having an outlet at its distal end. The distal end of the device is arranged to be inserted through the puncture or other opening. In the situation where the puncture is an artery or other blood vessel, the outlet of the tubular body is inserted through the puncture so that the distal end of the device is located within the blood vessel. An anchor is disposed within the tubular body and is oriented so that it is held in a compact aligned or compressed configuration within the tubular body prior to use. The tubular body also includes an ejector in the form of a plunger-like member arranged to force the anchor out of the outlet into the portion of the being's body generally contiguous with the opening, e.g., within the interior of the blood vessel, whereupon the anchor is unfolded or expands to form an enlarged tissue engagement surface.

A retraction filament is disclosed as being secured to the anchor or closure to enable it to be pulled fully along or adjacent to the puncture after the device's tubular body has been withdrawn so that the engagement surface of the anchor or closure intimately engages or abuts the inner surface of the tissue along the puncture.

In accordance with one aspect of the disclosure of the Kensey patents, the filament is held taut or otherwise secured and placed along the surface of the patient's skin to hold the anchor or closure in position in the puncture. Preferably, the anchor or closure and the associated filament are each formed of a biodegradable material. When the anchor or closure is used for sealing punctures or incisions in blood vessels it is disclosed as being constructed so that when it is open (i.e., in its unfolded or expanded state) and in position to seal the puncture, it doesn't appreciably block the flow of blood through the blood vessel.

In U.S. Pat. No. 4,890,612 granted to Kensey, there is disclosed a further closure device for sealing a puncture or incision formed percutaneously in tissue separating two internal portions of the body of a living being and a various methods of use for that device are also disclosed. The closure device of this Kensey invention is generally in the form of a holding member, a filament, and a sealing member. The holding member is an elongated body, constructed like a toggle, and preferably formed of a biodegradable material, such as a thermoplastic polymer or polyglactide. The toggle is disclosed as being molded onto the distal end of the filament. The filament is also biodegradable, and is preferably formed of polyglactide suture material. The flexibility of the filament enables the toggle to pivot to various orientations with respect to the suture and the sealing member. The sealing member basically comprises a cylindrical plug, preferably formed of a compressed foam or other material, that is highly absorbent and which when disposed within the body swells in excess of its compressed diameter.

The closure device of this Kensey patent is arranged to be used with an insertion instrument to place the closure device within the puncture or incision to be sealed. The insertion instrument includes a tubular body member in which closure device is positioned such that the holding member is oriented with its longitudinal axis parallel to the longitudinal axis of the tubular body member. When so disposed, the holding member may compress a portion of the distal end of the sealing member. The filament member extends backward from the holding member through or along the sealing member.

The insertion instrument of this Kensey patent is introduced into the puncture or incision in the artery or any body tissue (e.g., the liver, gall bladder, lung, heart, etc.) until its distal outlet is at the desired position in the body of a patient. When this instrument is used for sealing an artery, the outlet of the insertion instrument is positioned so that it is within the artery. The insertion instrument is then operated to expel the holding member from the tubular member. Once the holding member is expelled, the instrument may be held in this position for a short period of time to allow the foam at the tip of the sealing member, that is the distal end portion of the closure device, to swell. This action effectively tilts the holding member. The insertion instrument may then be withdrawn and the closure device's filament retracted. This action pulls the closure device's sealing portion back through the puncture or incision in the artery wall until the holding portion engages the inner surface of the artery wall to stop further retraction. As the holding member comes into engagement with the arterial wall, it may effect the compression of the distal end portion of the sealing member. Moreover, the proximal end portion of the sealing member extends into the puncture or incision in the subcutaneous tissue to a point closely adjacent to the skin. These actions effectively seal the puncture or incision from the passage of blood therethrough.

The patent literature also includes various other devices for closing an opening in a blood vessel or other opening. PCT Publication No. WO 90/14796 discloses the use of an occlusion member and a locking member which are oriented across the wall of the blood vessel to seal the incision from the flow of blood therethrough. In U.S. Pat. No. 5,108,421 granted to Fowler, a plug type member is disclosed along with one or more methods of inserting the plug into an incision. Other means and techniques for closing a wound or other incision are disclosed in U.S. Pat. No. 4,606,337 granted to Zimmermann et al. and in U.S. Pat. No. 5,053,046 granted to Janese.

Despite all of the relatively recent interest in this area, there is still a need for a simple and reliable means for effecting the closure of an opening, such as in the wall of a blood vessel, duct or lumen, by plugging the opening with a gelatinous material or similar hemostatic material and an anchor or similar assembly without requiring the application of manual pressure to the incision for an extended period of time.

SUMMARY OF THE INVENTION

Accordingly, it is a general object of the present invention to provide an assembly which overcomes the disadvantages of the prior art.

It is a further object of the present invention to provide a closure assembly that is effective for sealing a puncture or other opening in a blood vessel, duct or lumen without the need for the application of manual pressure thereto and without resulting in a significant reduction in the flow of blood through the blood vessel.

It is still a further object of the present invention to provide an insertion instrument that is simple in construction and which may be reliably inserted into a blood vessel, duct or lumen to position an anchor member or other closure therein for temporarily hemostatically sealing the puncture and then injecting a gelatinous or other hemostatic material, such as a fibrin type of tissue glue, into the incision to economically and simply seal the incision.

It is yet another object of the present invention to provide a closure assembly which is completely absorbable in the body of the patient within a relatively short period of time and which will allow the patient to be ambulatory shortly after the insertion of the closure assembly.

These and other objects of the present invention are achieved by providing an overall assembly for sealing an opening in the wall of a blood vessel, duct or lumen of a living being. The insertion assembly includes an insertion instrument having a tubular body for receipt of the closure assembly therein. The closure assembly is arranged to be expelled from the tubular body. The tubular body is generally formed by an elongate tubular member having a proximally located portion and a distally located portion. The distally located portion has an end with an opening therein and which is arranged to be introduced through the opening in the vessel, duct, lumen or other body cavity.

The closure assembly of the present invention preferably generally includes an anchor member, a gelatinous or similar material which forms a sealing means, and a filament member. The anchor member includes a tissue engaging portion and is configured to pass through the opening in one direction, but is resistant to passage therethrough in the opposite direction. The sealing means includes a gelatinous material, such as a tissue glue, including a cyanoacrylate, or fibrin material which engages the filament member as the gelatinous material dries or cures. The filament member is an elongate member that is preferably formed of a suture material having a length which is sufficient to be connected between the anchor member and the sealing means while extending across the wall of the vessel, duct or lumen.

The method of use of the present invention includes manipulating the carrier or insertion assembly and the anchor member to initially locate the anchor member within the carrier adjacent to the free or open end thereof. The open end of the insertion assembly is introduced through an introducer sheath into the opening in the vessel, duct or lumen of the patient and the anchor member of the closure assembly is then expelled from the open end of the insertion assembly. Thereafter the insertion assembly is operated to draw the tissue engaging portion of the anchor member into engagement with the tissue that is generally contiguous with the opening in the patient so that the tissue engaging portion of the anchor member at least initially or temporarily seals the opening from the flow of fluid from the vessel, duct or lumen therethrough.

The insertion assembly of the present invention also preferably includes a means for injecting a gelatinous material into the incision adjacent to the vessel, duct or lumen and along the filament member to enable the injection of the gelatinous material such as a fibrin glue into the incision proximally of the anchor. This portion of the insertion assembly may include one or more plunger members as part of an integral or separate syringe assembly to allow the gelatinous material to be injected into the incision once the anchor and filament member are positioned along the vessel, duct or lumen. The use of the gelatinous material has the advantage of functioning as a bioabsorbable tissue glue which engages the filament member to retain the anchor and filament member securely in position in the incision and retain the anchor member along the vessel, duct or lumen shortly after the gelatinous material is injected into the incision or puncture. In this invention it is believed that the anchor member is primarily needed to provide a temporary seal of the puncture or incision, i.e. until the gelatinous material sets up or cures. Therefore, the anchor member may be formed of a material that dissolves in a relatively short period of time and which is preferably equal to or less than the dissolution time of the resorbable anchor member disclosed in the various Kensey patents. Additionally, the composition of the gelatin material may optimally be varied at bedside according to the needs of each patient. For example, the composition of the gelatinous material may be adjusted to cure faster or slower depending on the amount of anticoagulants received by the patient during the procedure. Similarly, the invention disclosed herein is believed to be significantly less complex and less expensive to manufacture than various other sealing devices which have previously been proposed.

BRIEF DESCRIPTION OF THE DRAWINGS

Other objects and many of the attendant advantages of this invention will readily be appreciated as the same becomes better understood by reference to the following detailed description when considered in connection with the accompanying drawings wherein.

DETAILED DESCRIPTION OF THE PREFERRED FORMS OF THE PRESENT INVENTION

Figure 1:
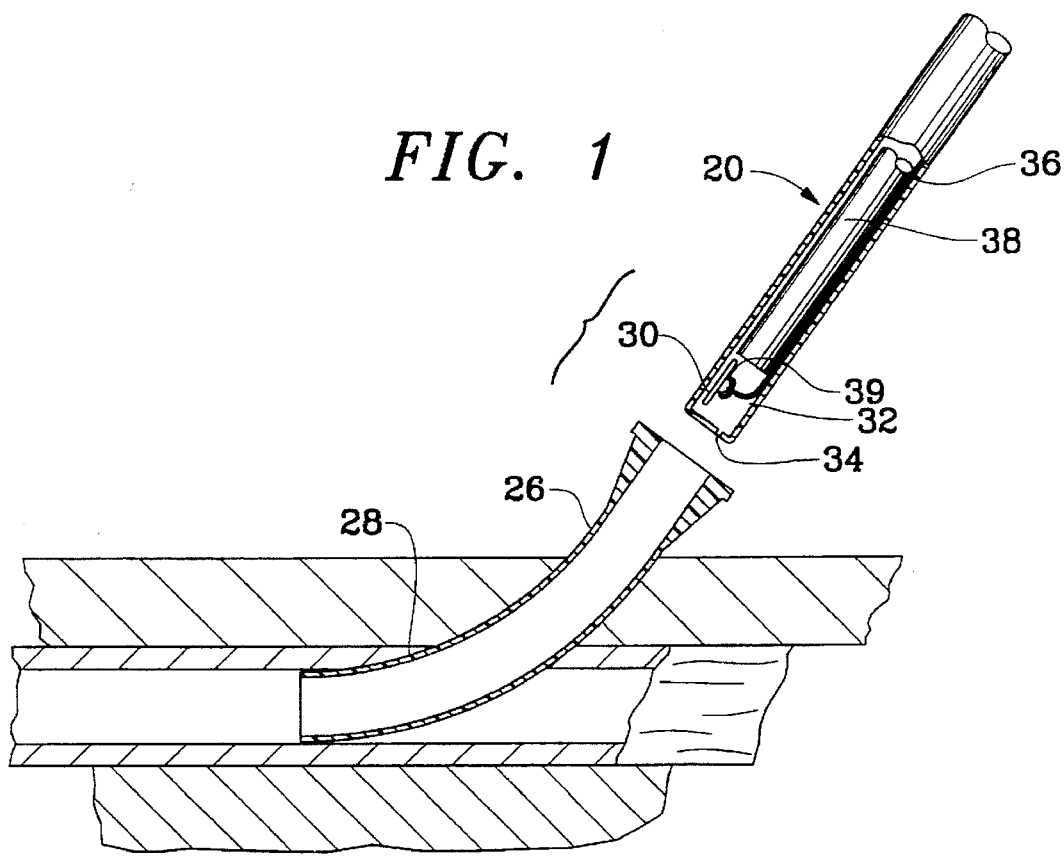
FIG. 1 is a side elevational view, partially in cross section, of a sealing device constructed in accordance with this invention for introducing an anchor member constructed in accordance with this invention into the body of a living being to seal an opening therein.

Referring now in greater detail to the various figures of the drawings wherein like reference characters refer to like parts, there is shown generally at 20 in FIG. 1, a device for effecting the closure of an incision, puncture or other opening in a blood vessel, duct or lumen of a living being. The device 20 has particular utility when used in connection with intravascular procedures, such as angiographic dye injection, balloon angioplasty and other types of recanalization of atherosclerotic arteries, in situ valvulectomy, etc. However, it should be appreciated that the device 20 can be used to hemostatically close a puncture or other opening in other types of vessels, ducts, lumens or body cavities within the body of a patient, such as in various laparoscopic, arthroscopic or other procedures. Thus, it is to be understood that while the description of the invention as contained herein is described with respect to the closure of percutaneous punctures in blood vessel such as arteries, the device 20 of the present invention has many more applications or uses. As used herein, the term "gelatinous" is intended to include a material having a wide range of viscosity such as a slightly viscous material, a suspension or a paste.

Before describing the overall device 20, a brief description of a typical, conventional, intravascular surgical procedure, e.g., catheter instrumentation of an artery, utilizing a percutaneous incision or puncture will be given to best appreciate the features of the device 20. In such a procedure, a cannula such as an angiographic needle (not shown), is inserted percutaneously through the skin into the artery, such as the femoral artery 24 at the desired location for the instrument's insertion. The needle cannula is held in place and the flexible end of a mini-guidewire (not shown) is then passed through the cannula into the artery to the desired depth (i.e., a longitudinal position therealong). Once the mini-guidewire is in place, the needle cannula is removed leaving the guidewire in position. A conventional introducer sheath 26 and an arterial dilator (not shown) are then passed over the guidewire through the puncture 28 and into the artery 24. The guidewire and the dilator are then removed leaving the sheath 26 in place. The catheter (not shown) or other intravascular instrument is then inserted through the introducer sheath 26 and threaded down the artery to the desired intravascular location, e.g., the location of an atherosclerotic occlusion. Once the intravascular procedure has been completed, the catheter or instrument is removed. Thereafter the sheath 26 may be removed and the surgeon or other trained professional has previously been required to apply manual pressure to the percutaneous puncture until hemostasis occurs. In many patients, this may require at least thirty minutes of manual pressure.

The device 20 of the present invention generally effects the hemostatic closure of a percutaneous or other type of puncture, incision or opening in an artery, other body duct or lumen without necessitating the application of manual pressure thereto. Thus, once the catheter or other intravascular instrument has been removed but with the sheath 26 preferably left in place, the device 20 of the present invention is inserted through the sheath 26 into the artery 24 and operated to expel a closure or anchor member 30 (to be described later) into the artery. The anchor member 30 is arranged to be drawn back generally adjacent to the wall of the blood vessel and adjacent to the puncture 28 to at least temporarily seal the incision from the flow of blood therethrough. A gelatinous and/or hemostatic material may then be injected into the puncture and the introducer sheath and insertion assembly are then removed. The anchor member and gelatinous material are then left in place to seal the puncture, incision or other opening from the flow of fluids therethrough. Due to their construction, the anchor member 30 and gelatinous material, as described broadly above, are preferably absorbed by the surrounding tissue in a relatively short period of time.

Referring now to FIGS. 1–9, further details of the preferred form of the anchor member 30 will now be discussed. The anchor component or member may comprise a relatively thin, narrow strip of material, such as a resorbable lactide/glycolide polymer sold by E. I. DuPont de Nemours, Inc. under the trade designation MEDISORB. The anchor member 30 is sufficiently rigid such that once it is in position within the artery it is resistant to deformation to preclude it from bending and thus passing back through the puncture or incision through which it was first introduced, yet is sufficiently flexible or pliable to conform generally to the shape of the interior of the artery so as not to injure the arterial tissue. The body portion of the anchor member 30 preferably includes at least one aperture located at the approximate middle of the anchor member 30 and through which a portion of the filament member 36 extends.

The anchor member 30 may also be an unfoldable or expandable member which, when contracted or compressed, is sufficiently compact to fit within the interior of the tubular body 32, but when unconstrained by the tubular body 32 it may expand or unfold to an enlarged configuration suitable for closing off the puncture 28 generally along the artery. Thus, the anchor member 30 may be generally formed of a resilient and/or hemostatic material that is preferably biodegradable and/or resorbable, so that it will be absorbed within the body of the patient after a relatively short period of time. One potentially effective material for an alternate form of the anchor member 30 may be a porous hemostatic absorbable gelatin sold by Johnson & Johnson, Inc. under the name GELFOAM.

Figure 3:
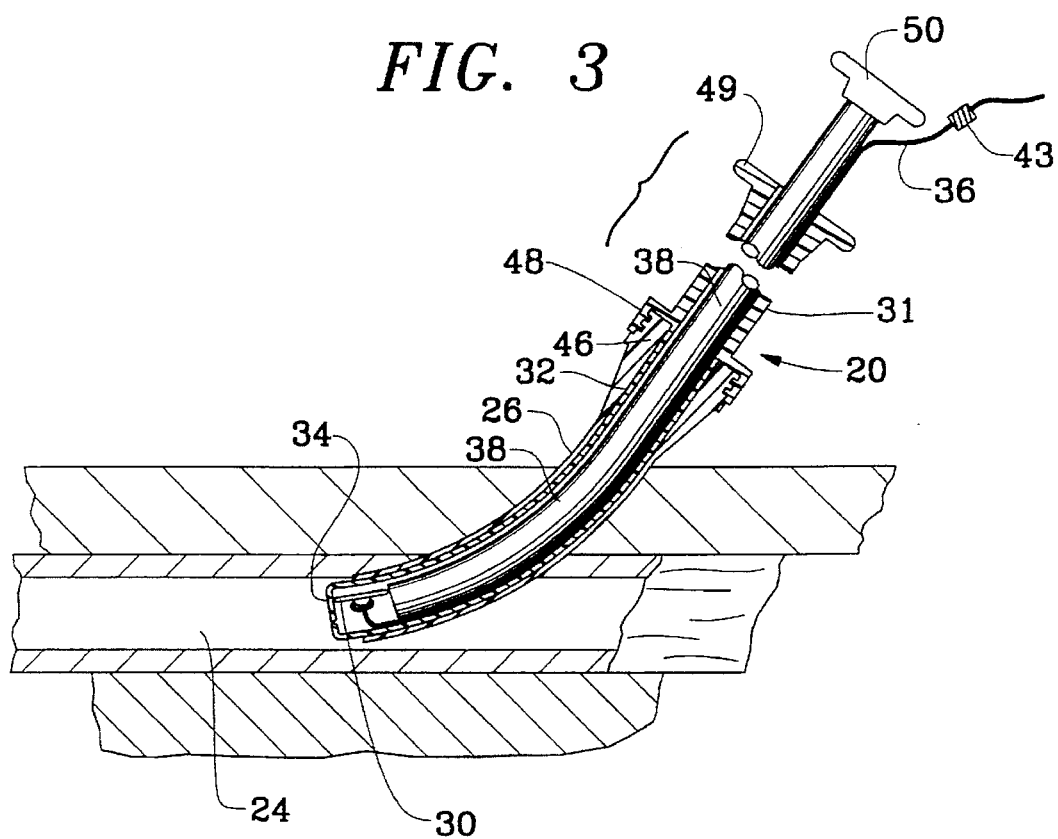
FIG. 3 is an enlarged side elevational view, partially in cross section, showing the insertion assembly inserted into the introducer sheath and positioned in the vessel of the patient.

The filament member 36 preferably constitutes an elongated flexible thread, which may be formed of a long, yet very thin, biodegradable material, such as an absorbable suture, and which is preferably fixedly or otherwise secured to the proximal side or surface of the anchor member 30. Additionally, the filament member 36 may also preferably include a crimp stop member 43 thereon as shown in FIG. 3. The crimp stop 43 is preferably a metal member which is fixedly attached to the filament member 36 at a predetermined distance from the anchor member 30. Although the filament member 36 is described herein as an elongated flexible member, it should be appreciated that a semi-rigid or other suitable member may also be used as the filament member so long as the anchor member 30 is securely associated therewith and the gelatinous material is able to bond or otherwise engage the filament member to obstruct the flow of fluids through the incision, puncture or other opening.

In the preferred forms of the present invention, the filament member 36 is preferably long and thin; and, therefore, the filament member 36 does not interfere with the operation of the plunger member 38 as the plunger member 38 is actuated to expel the anchor member 30 out of the distal outlet 34 as described more fully below. Furthermore, the plunger member 38 and/or portions of the filament member 36 may be modified to accommodate the desired thickness and shape of the filament member 36 as well as the route of passage of the filament member 36 through the tubular body 32. Therefore, as the anchor member 30 is expelled into the artery, the filament member 36 slides down the tubular body 32 either along or through the plunger member 38. The length of the filament member 36 is sufficiently long so that a substantial portion of the filament member 36 extends outside of the proximal end of the device 20 even after the anchor member 30 is properly positioned in the artery to enable the tubular body 32 to be withdrawn from the incision without interfering with the application of tension to the filament member 36. The coupling of the filament member 36 to the anchor member 30 may be effected in various ways to achieve any desired "mechanical advantage" to ensure that the anchor member 30 is securely retained on the filament member 36 and to provide consistent deployment of the anchor member 30 along the wall of the blood vessel adjacent to the incision.

As shown generally in the drawings, the gelatinous material 52 may be injected into the incision once the anchor member 30 is positioned in the desired location, such as adjacent to the wall of the vessel, lumen or duct. In a preferred form of the present invention, the gelatinous material 52 may consist of a bioabsorbable and preferably hemostatic material such as a fibrin glue which may include two primary components. Alternately, the gelatinous material 52 may be formed of a single component material such as cyanoacrylate. The gelatinous material 52 is also preferably curable in the body of the patient and/or otherwise formed to react with the body fluids of the patient to form a gel-like mass of material which adheres to the filament member 36 to promote hemostasis in the incision or puncture 28 and which secures the anchor member 30 along the wall of the blood vessel.

Figure 8:
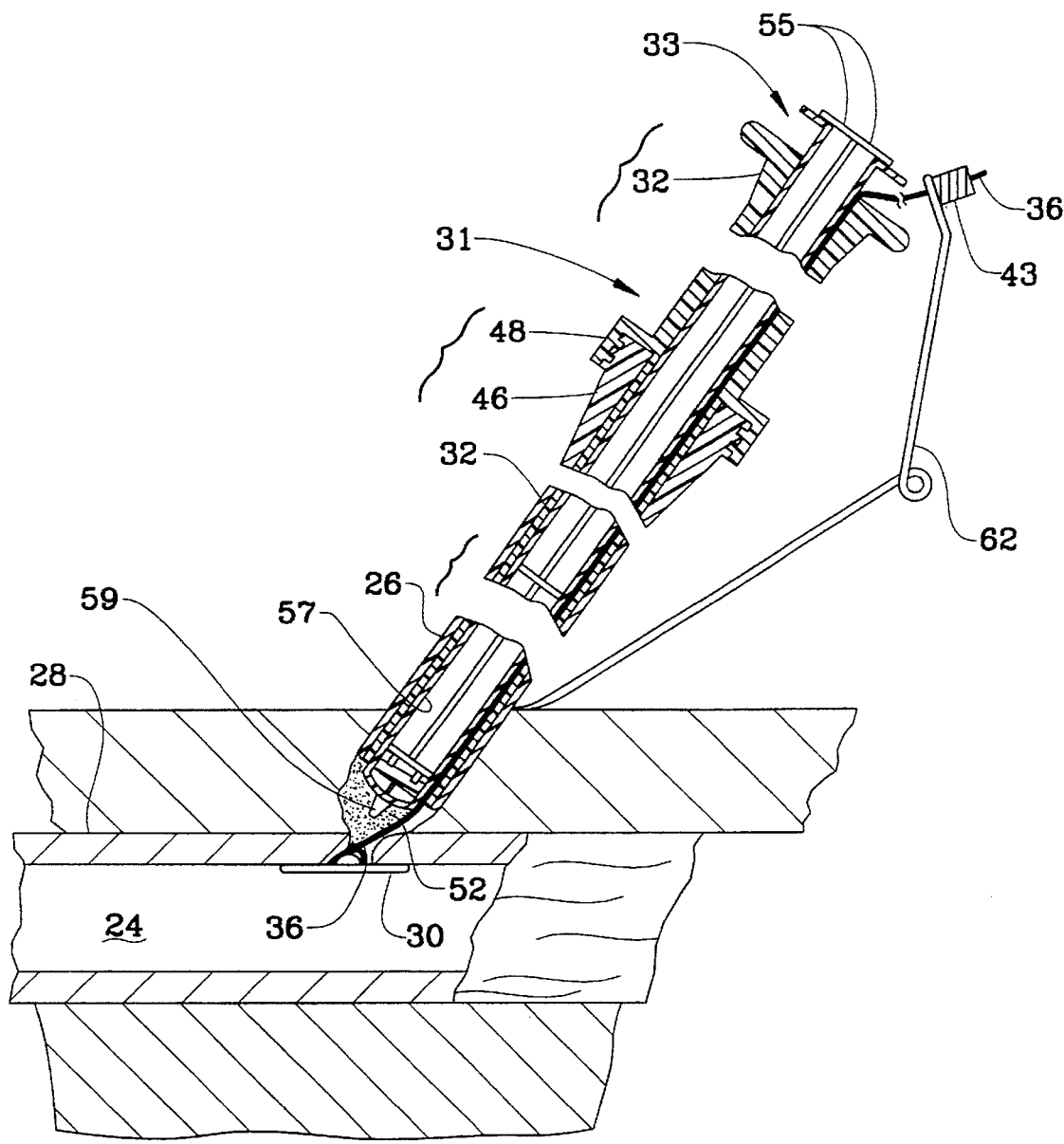
FIG. 8 is a side view, partially in cross section, showing the injection of the gelatinous material into the puncture.
Figure 12:
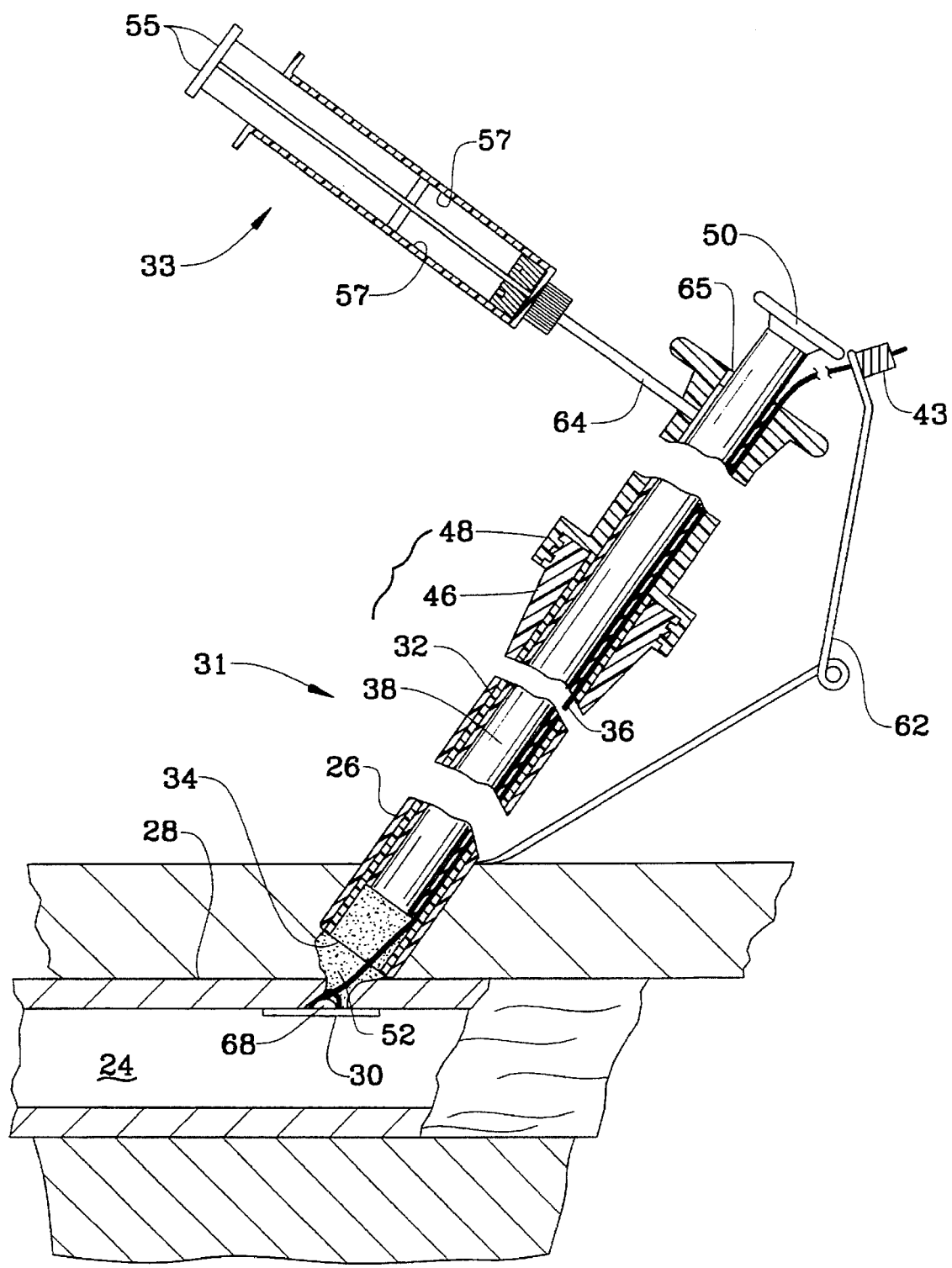
FIG. 12 is a side view, partially in cross section, showing the plunger member in the insertion assembly of the embodiment shown in FIG. 10 in the extended position.

The first preferred component of the fibrin glue may be a fibrinogen material 54 which may be supplied in a solution or as a powder which is to be reconstituted prior to use. The second preferred component of the fibrin glue may be a thrombin material 56 which may also be provided to the physician in a solution or powder such that both components may be injected into the incision as described below. Due to the rapid rate of fibrin clot formation with these components, they are preferably separately injected into the incision such that the fibrinogen and thrombin materials are not mixed until they reach the desired location in the incision. One way to overcome the problems associated with the rapid clot formation of these components is through the use of a dual plunger syringe assembly 33, an example of which is shown in FIGS. 8 and 12. This type of syringe assembly 33 may include a common or parallel outlet to ensure that the components are not mixed prematurely thereby potentially causing a clot to form in the delivery device prior to use. The use of the fibrinogen and thrombin materials, 54 and 56 respectively, are believed to be advantageous because the thrombin 56 converts the fibrinogen 54 to fibrin by an enzymatic action at a rate which is determined by the concentration of thrombin. Therefore, the relative concentrations of the fibrin 54 and thrombin 56 solutions may be varied to increase or decrease the rate of clot formation so that if equal concentrations of fibrinogen and thrombin form a fibrin clot in a matter of seconds, a more dilute concentration of thrombin may be used to form a fibrin clot in a few minutes.

In a fibrin sealant kit which is presently available from the Scottish National Blood Transfusion Service for use in clinical trials only, the fibrinogen 54 is provided as a lyophilized friable solid material containing 225 mg of fibrinogen and approximately 50 units of factor VII. The solvent supplied for reconstitution of the fibrinogen 54 consists of 20 mM Tris buffer with a pH of 7.5 and containing aprotinin at 3000 kallikrein inactivator units per milliliter. The thrombin 56 is supplied as a friable lyophilized solid containing 1000 IU per vial. The thrombin 56 is reconstituted with a calcium chloride solution containing about 40 mM of calcium chloride.

In whatever relative concentration of fibrin 54 and thrombin 56 that is used, it is believed that the present invention is an improvement over currently proposed hemostatic devices because the rate of clot formation may be adjusted by the physician as needed and according to a variety of factors including the requirements of the individual patient.

The foregoing describes the preferred form of the basic components of the present invention while the following describes the preferred form of the various devices and methods used to insert the anchor member 30 and the gelatinous material 52 into their respective desired locations in the body of the patient to seal the incision, puncture or opening in the vessel, duct or lumen. In the event that a single component gelatinous material is used, the syringe assembly 33 may be a conventional single chamber syringe, and the insertion technique may be modified accordingly.

A basic form of the present invention is shown in FIGS. 1–9. The device 20 of this embodiment generally includes an insertion assembly 31 which may consist of a simple delivery device such as an elongate tubular body 32. The insertion assembly may also include a plunger member 38 associated therewith. The tubular body 32 and the tubular body 32 and plunger member 38 combination of the insertion assembly 31 serve as a relatively simple means to deliver the anchor member 30 to the desired location in the body of the patient. The syringe assembly 33 preferably includes a pair of plunger members 55 located in a pair of separate chambers 57 although it is anticipated that separate syringes may be used to inject the materials into the incision. As will be described more fully below, a variety of delivery means are believed to satisfy the need to accurately deliver the sealing components of the present invention with the primary difference between the respective delivery means being related to the complexity of the insertion assembly 31 and the syringe assembly 33. Whatever insertion assembly 31 and syringe assembly 33 combination are chosen, it is important that the anchor member 30 and gelatinous material 52 be consistently and reliably positioned in their desired locations in the incision, puncture or other opening and along the vessel, duct or lumen of the patient because it very important that the gelatinous material not be injected into the blood vessel.

Figure 2:
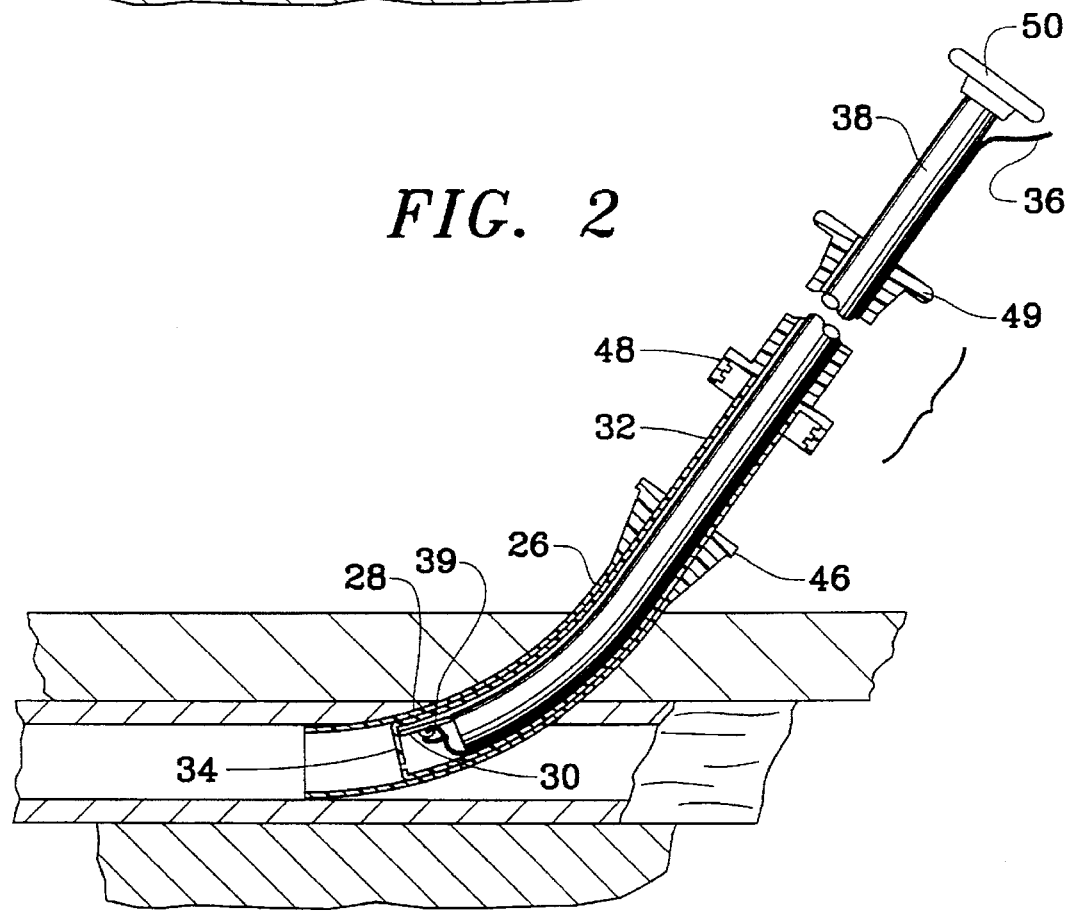
FIG. 2 is a side elevational view, partially in cross section, showing the insertion assembly and introducer sheath of FIG. 1 with the tubular body partially inserted into the introducer sheath.

FIG. 1 is illustrative of one basic form of the insertion assembly 31 of the present invention. The insertion assembly 31 preferably includes a simple tubular body 32 having an outlet 34 at its distal end and a plunger member 38 disposed in the tubular body 32. The tubular body 32 is an elongate tubular member preferably having a relatively small outside diameter, e.g., in the range of about 6 french to 14 french, and formed of a somewhat flexible material, such as a polyethylene or polyvinylchloride, to allow the tubular body 32 to be inserted through an introducer sheath 26 into the artery 24 or through the incision after the introducer sheath 26 has been removed. As shown in FIG. 2, the length of the tubular body 32 is preferably sufficient to position the outlet 34 of the tubular body 32 adjacent to or slightly beyond the distal end of the introducer sheath 26 when the tubular body 32 is fully inserted therein.

The plunger member 38 basically comprises a simple elongated, cylindrical rod-like member, having a relatively flat distal end 39 thereon. As with the tubular body 32, the plunger member 38 is also formed of a relatively flexible material, such as polyethylene or polyvinylchloride and is sized to be disposed within the interior of tubular body 32. The outside diameter of the plunger member 38 is slightly less than the inside diameter of the tubular body 32 to enable the plunger member 38 to be manually movable along the longitudinal axis of the tubular body 32 and to push or force the anchor member 30 out of the distal outlet 34 while allowing the filament member 36 to pass therebetween. Thus the plunger member 38 is arranged to be moved from a retracted position, as shown in FIG. 2 to an extended position (FIG. 3) wherein the distal end 39 of the plunger member 38 is located adjacent to the distal outlet 34 of the tubular body 32. When the plunger member 38 is moved to the extended position, the distal end 39 of the plunger member 38 forces the anchor member 30 out of the outlet 34 and into the artery as described below.

The preferred operation of the present embodiment of the present invention is best understood by sequential reference to FIGS. 1–9. The device 20 may be initially inserted into the introducer sheath 26 so that the distal outlet 34 of the tubular body 32 extends through the incision or puncture 28 and into the blood vessel, duct or lumen of the patient as shown in FIG. 3. The device 20 may then be secured to the sheath 26 by coupling the threaded luer lock 46 from the sheath 26 with the luer lock 48 of the tubular body 32. As shown in FIG. 2, the proximal end of the tubular body 32 may be in the form of an annularly projecting flange 49 to serve as a handle to enable the user to grasp the insertion assembly 31 with their fingers to eject the anchor member 30 as described below.

Figure 4:
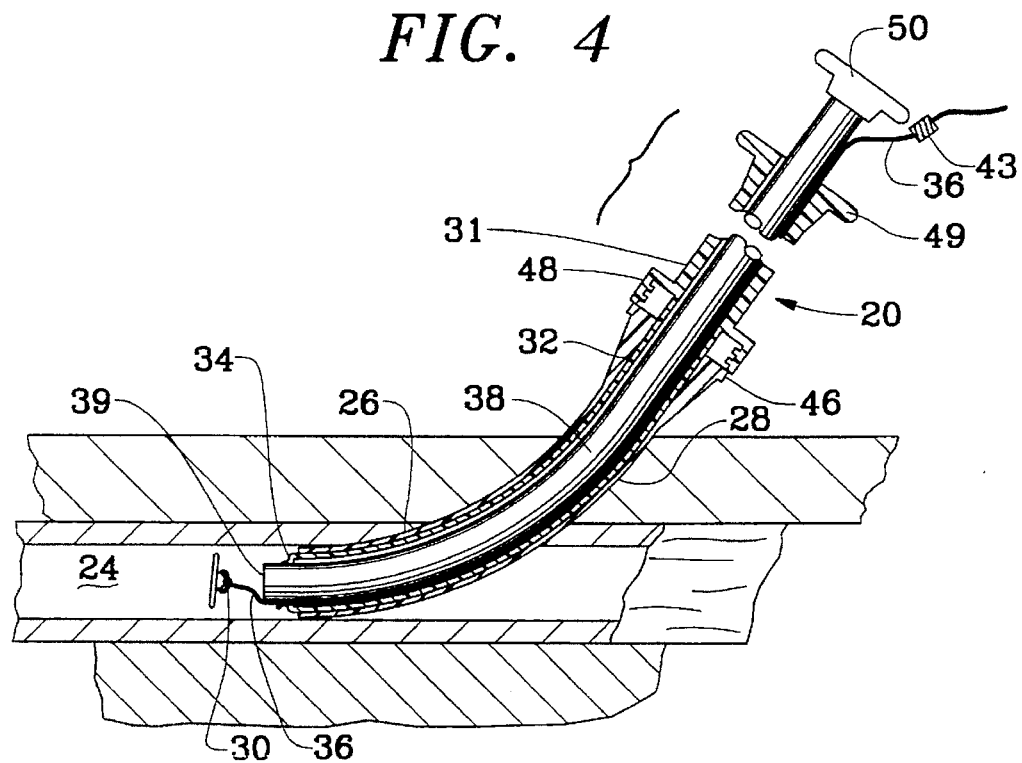
FIG. 4 is a side view, partially in cross section, showing the introduction of the anchor member into the vessel of the patient.

Once the tubular body 32 and sheath 26 are interconnected as shown in FIG. 3, the user may then engage and depress the proximal end cap 50 of the plunger member 38 with their thumb, while grasping the flange 49 of the tubular body 32 between their fingers. This action slides the plunger member 38 in the distal direction within the sheath 26, whereupon the distal end 39 of the plunger member 38 contacts the proximal portion of the anchor member 30 of the closure assembly. Continued depression of the plunger member 38 towards the tubular body 32 forces the anchor member 30 to slide down the interior of the tubular body 32 towards the distal outlet 34. At the point that the distal end 39 of the plunger member 38 reaches the distal outlet 34 of the tubular body 32, an audible "signal" may be produced by nearly any conventional means (not shown) to signal that the plunger member 38 has pushed the anchor member 30 out through the tubular body's 32 distal outlet 34 and into the interior of the artery 24 as shown in FIG. 4.

Figure 5:
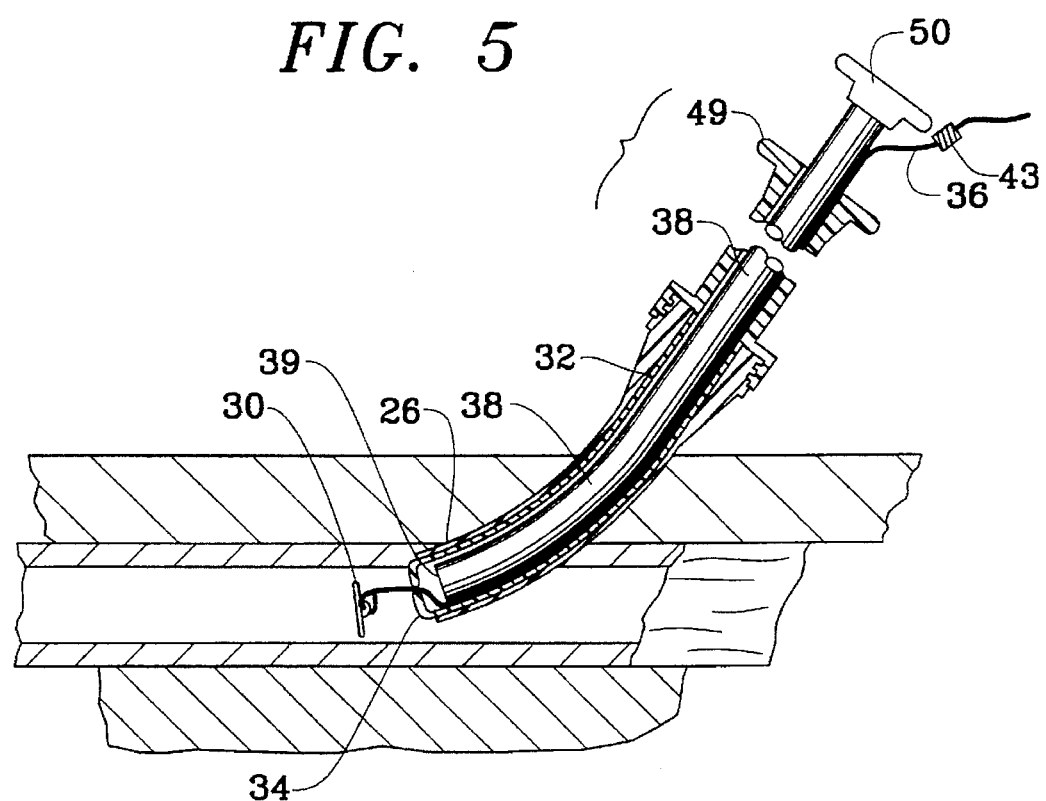
FIG. 5 is a side view, partially in cross section, showing the anchor member drawn into contact with the distal outlet of the insertion assembly.
Figure 6:
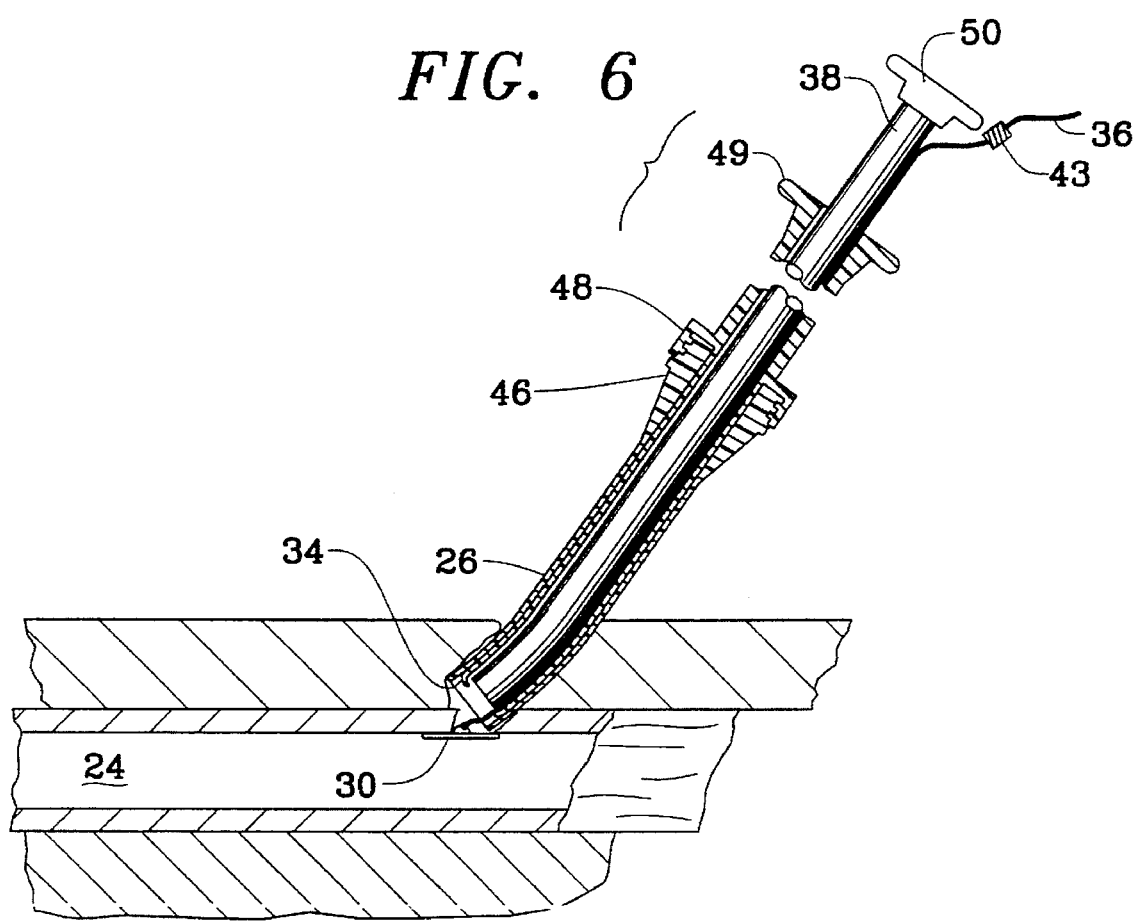
FIG. 6 is a side view, partially in cross section, showing the withdrawal of the insertion assembly in the puncture with the anchor member in contact with the wall of the vessel.
Figure 7:
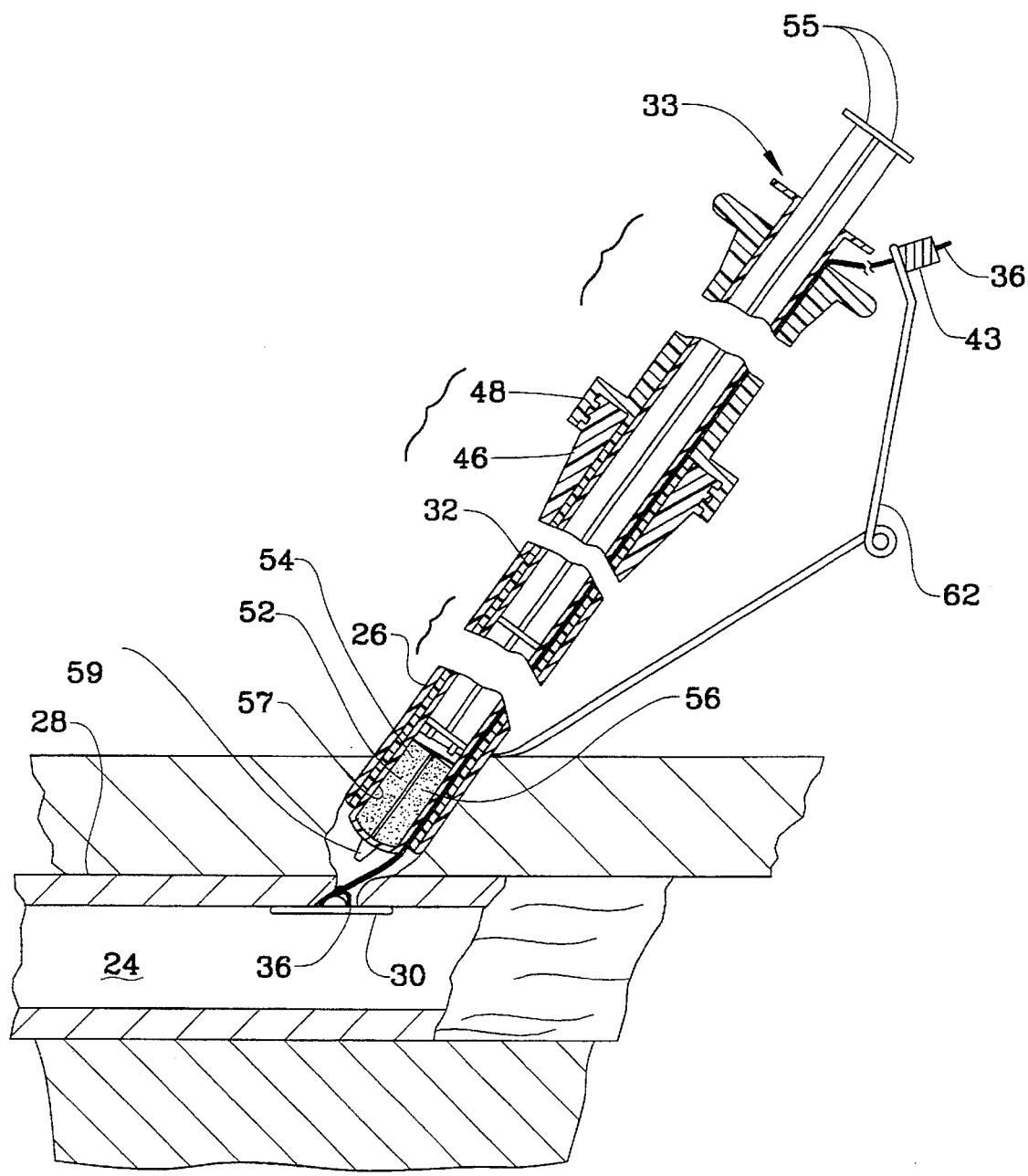
FIG. 7 is a side view, partially in cross section, showing the syringe assembly inserted into the partially withdrawn insertion assembly and the spring member attached between the filament member and the skin of the patient.

The distal outlet 34 of the tubular body 32 may preferably include a plurality of petal-like, curved projections 51 which are equidistantly spaced about the periphery of the tubular body 32 to form a one-way, openable gate or distal outlet 34 through which the anchor member 30 is ejected when the insertion assembly 31 is used. Once the anchor member 30 has been ejected past the distal outlet 34 and into the artery, the user may allow the anchor member 30 to soften slightly by allowing the anchor member 30 to remain suspended in the artery 24 for a few seconds. Next, the user may grasp the filament member 36 to draw the anchor member 30 into contact with the distal outlet 34 of the tubular body 32 such that the anchor member 30 blocks the distal outlet 34 of the tubular body 32 as shown in FIG. 5. The user may then withdraw the sheath 26, the tubular body 32 and the anchor member 30 together until the anchor member 30 contacts the wall of the artery 24 adjacent to the puncture 28 as shown in FIG. 6. Next, a tensioning member such as a leaf or similar spring member 62 may be used to apply a steady pressure to the filament member 36 to retain the anchor member 30 in the desired position adjacent to the wall of the artery 24. As shown in FIG. 7, the spring member 62 may be positioned between the crimp stop 43 and the skin of the patient so that the sheath 26 and the tubular body 32 are movable in combination with respect to the anchor member 30 and the filament member 36 without altering the position of the anchor member 30. At this point in the procedure, it may be desirable to withdraw the sheath 26 and the tubular member 32 slightly with respect to the anchor member 30 so that the distal outlet 34 of the tubular member 32 is spaced apart a short distance from the anchor member 30 and is withdrawn into the incision slightly proximal of the wall of the blood vessel.

In this position, the anchor member 30 temporarily seals the incision from the flow of blood through the artery. The plunger member 38 may then be removed from the tubular body 32 and a syringe assembly 33 is then inserted into the tubular body 32 as shown in FIG. 7. The syringe assembly 33 is preferably a generally conventional dual plunger syringe assembly. As shown in FIG. 7, the syringe assembly 33 generally consists of a pair of side by side plunger members 55 which are movable in separate chambers 57 and open into a common outlet 59. The chambers 57 of the plunger assembly 33 contain the reconstituted fibrin and thrombin materials, 54 and 56, therein. As shown in FIG. 7, the syringe assembly 33 is sized to extend along the length of the tubular body 32 so that the outlet 59 of the syringe assembly 33 extends slightly beyond the outlet 34 of the tubular body 32.

Once the syringe assembly 33 is properly positioned in the tubular body 32, the user may simultaneously depress the plunger members 55 of the syringe assembly 33 to eject the fibrin and thrombin materials, 54 and 56, therefrom. As the fibrin and thrombin materials, 54 and 56, are ejected from their respective chambers 57, they are mixed together at the outlet 59 of the syringe assembly 33 as they enter the incision.

Figure 9:
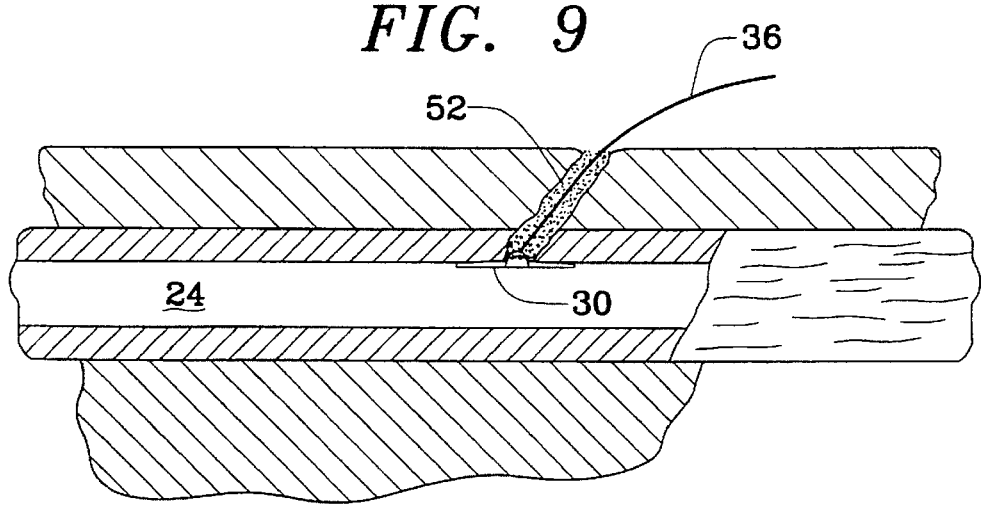
FIG. 9 is a side view, partially in cross section, showing the preferred positioning of the preferred embodiment of the present invention.

As shown in FIGS. 8 and 9, the fibrin and thrombin materials are ejected from the syringe assembly 33 into the distal portion of the incision and proximally of the anchor member 30 to form a mass of the gelatinous material 52. The gelatinous material 52 is positioned in the incision proximally of the anchor member 30 and/or the wall of the blood vessel. As the fibrin and thrombin materials, 54 and 56, are ejected from the syringe assembly 33, it may be desirable to withdraw the sheath 26 and tubular body 32 gradually from the incision 28 to spread the gelatinous material 52 along the tract of the incision. Additionally, because the incision extends through the wall of the blood vessel and other percutaneous or subcutaneous tissue, the tissue along the incision has a tendency to constrict or close as the syringe assembly is retracted. The wall of the blood vessel is formed of tissue similar to that of a muscle; and, therefore, the wall of the blood vessel constricts more quickly than the remainder of the incision. Therefore, the constriction of the tissue layers and the positioning of the anchor member 30 along the wall of the blood vessel cooperate to prevent the fibrin and thrombin materials from entering the blood vessel of the patient. Although the gradual withdrawal of the sheath 26 and tubular body 32 while the gelatinous material 52 is injected is desirable, it is not believed to be a requirement for the proper operation of the present embodiment and will depend on a number of factors, including the relative concentrations of the fibrin and thrombin materials as well the volume of gelatinous material 52 to be injected into the incision. It may also be desirable to leave the sheath 26 and tubular body 32 in place in the incision 28 for a short period of time to allow the gelatinous material 52 to begin curing before the incision is disturbed by the withdrawal of the sheath 26 and tubular member 32 as described more fully below. Finally, when the user determines that an adequate seal has been formed in the incision 28 and along the filament member 36, the spring member 62 may be released from the filament member 36 and removed from the skin of the patient. Next, the sheath 26 and tubular body 32 may be removed completely from the incision, and the portion of the filament member 36 extending beyond the skin of the patient may be cut leaving the incision sealed by the gelatinous material 52, anchor member 30 and filament member 36 as shown in FIG. 9.

As the gelatinous material 52 cures and forms a clot in the incision, the gelatinous material 52 frictionally engages the filament member 36 to ensure that the anchor member 30 is retained along the wall of the blood vessel. Additionally, the clot formed by the gelatinous material 52 will absorb any bleeding from the tissue surrounding the incision 28 and will also absorb any blood which may seep past the anchor member 30. Over the next few weeks, the gelatinous material 52, the filament member 36 and the anchor member 30 will be absorbed into the tissue of the patient.

The anchor member 30 functions to ensure that none of the gelatinous material 52 enters the artery and also to ensure that the gelatinous material 52 has an opportunity to cure without substantial amounts of blood or other fluids immediately diluting the fibrin and thrombin materials. Because the gelatinous material 52 is designed to form clots, it is very important that the gelatinous material not be injected or otherwise released into the blood vessel of the patient. Ultrasound pictures from a study of a hemostatic device having an anchor member 30 of the type generally described herein illustrate that an initial step in the healing process involves the encapsulation of the anchor member 30 along the wall of the blood vessel. Therefore, it is believed that with the present invention, it may be possible to restick the patient to form another incision near or at the prior incision site shortly after the original incision because the gelatinous material 52 may be formulated to be absorbed relatively quickly, and it is believed that the clot would not be adversely affected if it is repunctured before it is completely absorbed. In order to facilitate the repuncture of the patient, the anchor member 30 and/or the gelatinous material 52 may also be formulated to include a radiopaque material therein to assist the user in identifying the location of the prior incision 28.

Figure 10:
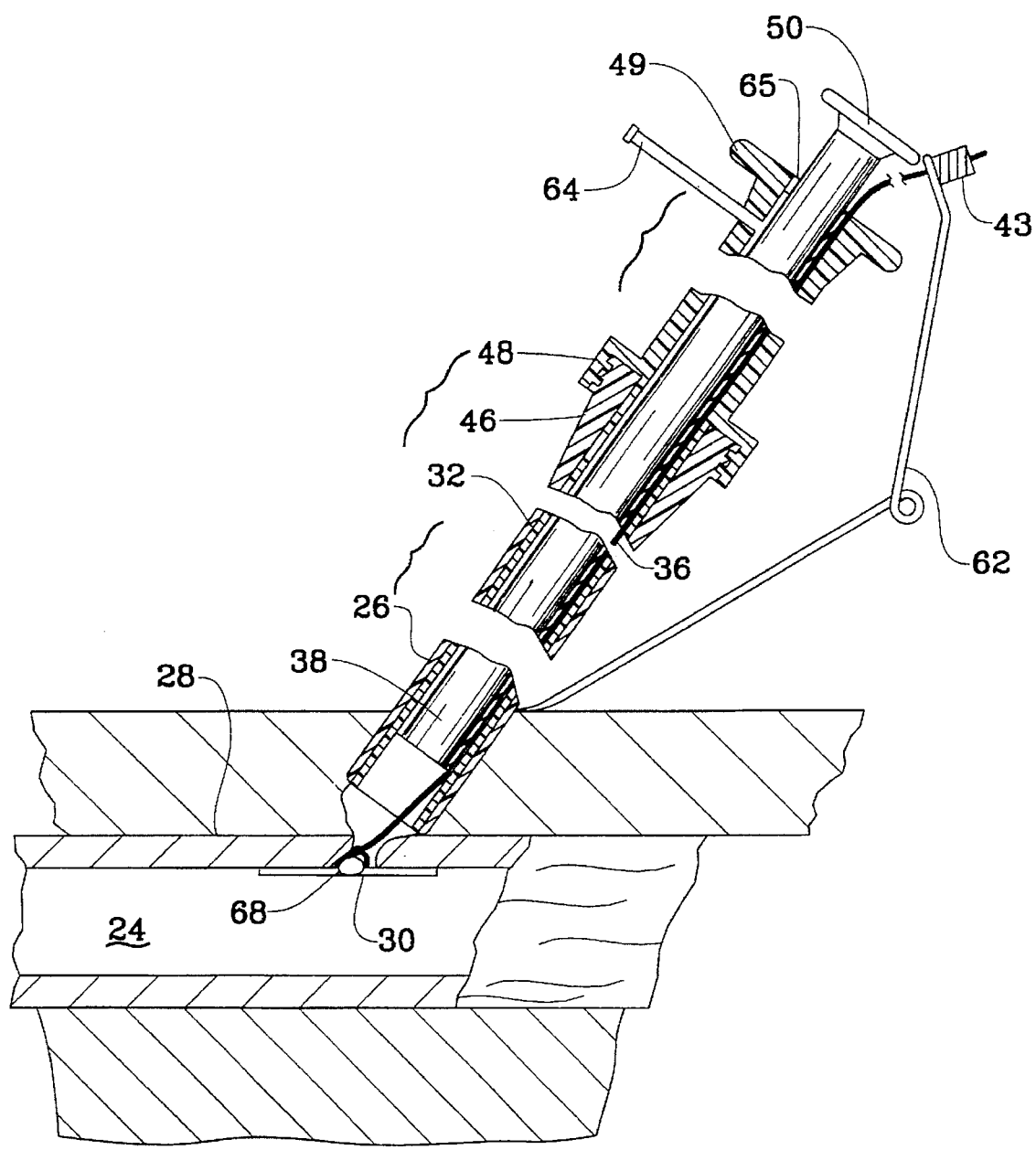
FIG. 10 is a side view, partially in cross section, of an alternative embodiment of the present invention.
Figure 11:
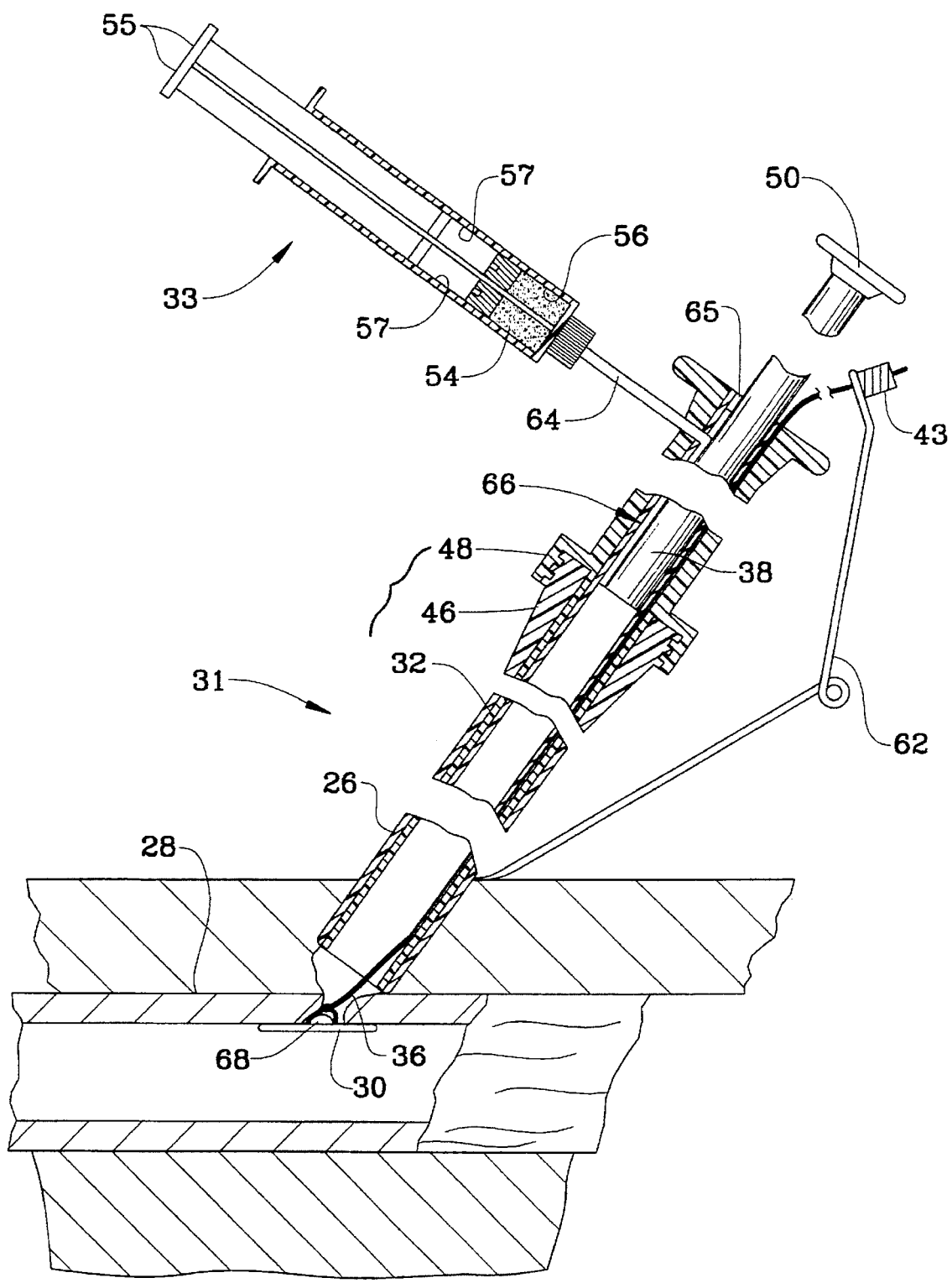
FIG. 11 is a side view, partially in cross section, showing the syringe assembly of the embodiment of the present invention shown in FIG. 10.

FIGS. 10 to 12 are illustrative of a further embodiment of the present invention where like numbers have been added to like members to illustrate the similarities between the respective embodiments. In this embodiment, the tubular member 32 includes one or more side openings or ports 64 along the proximal end thereof and a hemostatic valve 65 at the proximal end thereof. As shown in FIG. 10, the anchor member 30 is initially deployed in the manner described above with respect to the prior embodiment and shown in FIGS. 1–7. The side port 64 of the tubular body 32 is in flow communication with an outlet 66 which is located on the interior of the tubular body 32 as shown best in FIG. 11. Next, the plunger member 38 is retracted in the tubular member 32 to a location which is proximal of the outlet 66 on the interior surface of the tubular body 32. The user then connects the syringe assembly 33 to the side port 64 in the manner shown in FIG. 11. If conventional single chamber syringes are to be used, it may be desirable to use multiple side ports such that the thrombin and fibrin materials, 54 and 56, are not mixed until they are injected into the incision 28. In the embodiment shown, the dual chamber syringe assembly 33 includes the reconstituted thrombin and fibrin materials, 54 and 56, therein. Once the syringe assembly 33 is connected to the side port, the fibrin and thrombin materials may be ejected from the syringe assembly 33 and into the interior of the tubular body 32. The user may allow the thrombin and fibrin materials to cure for a short period of time in the tubular body 32, if desired. Next, the plunger member 38 of the tubular body 32 may be depressed and moved to the extended position as shown in FIG. 12 to eject the gelatinous material 52 into the puncture adjacent to the anchor member 30 and along the proximal side of the wall of the blood vessel.

As also shown in FIGS. 10 to 12, the anchor member 30 of the present embodiment may include an enlarged head member 68 which extends inwardly from the wall of the blood vessel when the remaining portion of the anchor member 30 is positioned along the wall of the blood vessel. With this type of anchor member 30, the gelatinous material 52 is able to coagulate around the head member 68 of the anchor member 30 to form a secure seal in the puncture. As with the anchor member 30 of the prior embodiment, the gelatinous material 52 also forms a clot around the filament member 36 to ensure that the anchor member 30 is securely retained adjacent to the wall of the blood vessel.

Figure 13:
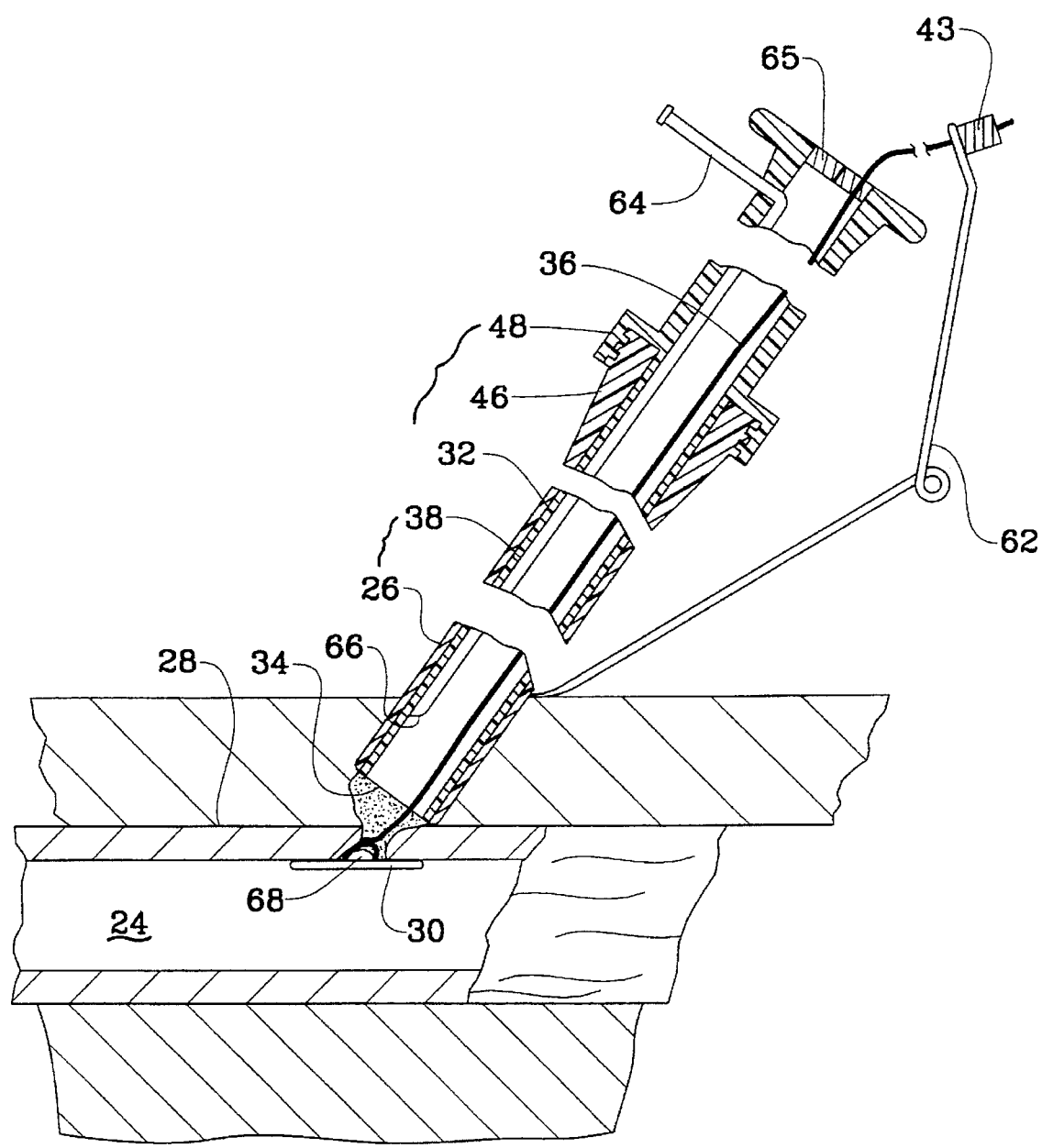
FIG. 13 is a side view of an alternative embodiment of the present invention similar to the embodiment shown in FIGS. 10-12 wherein the gelatinous material is injected through a port which opens near the distal end of the tubular member.
Figure 14:
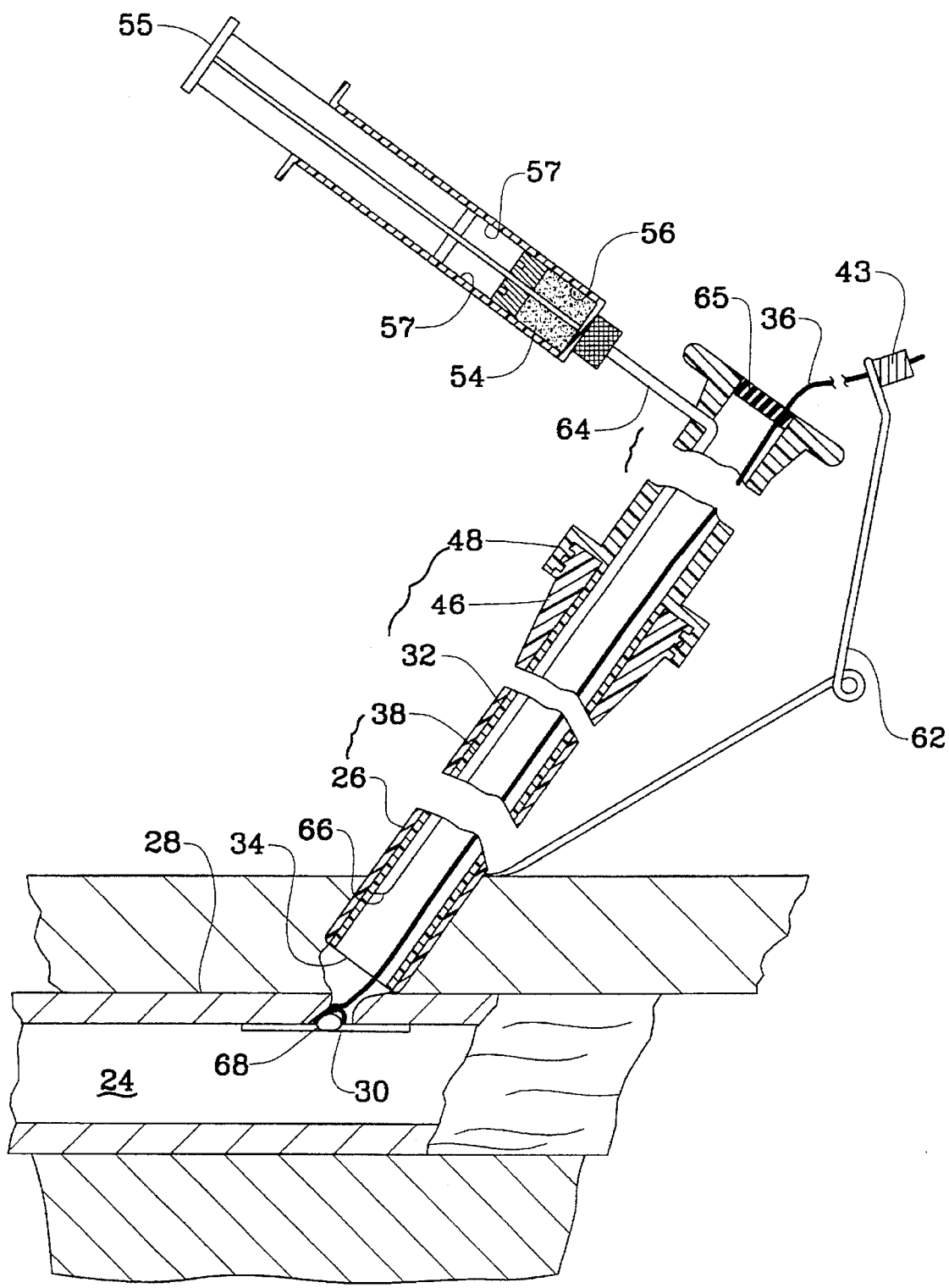
FIG. 14 is a side view, partially in cross section, showing the syringe assembly of the embodiment of the present invention shown in FIG. 13.
Figure 15:
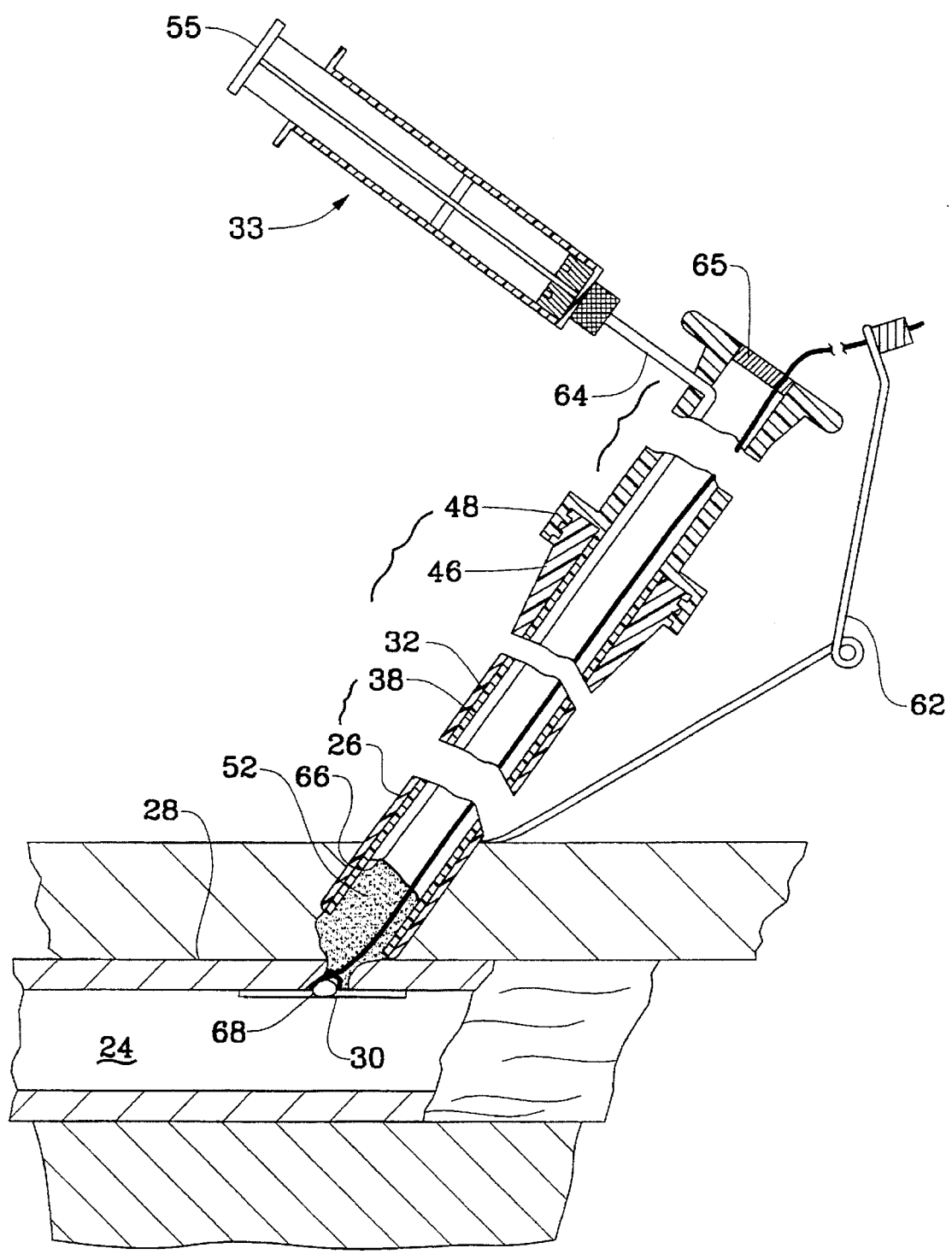
FIG. 15 is a side view, partially in cross section, showing the gelatinous material in the insertion assembly of the embodiment shown in FIG. 13 prior to removal of the tubular body from the incision.

FIGS. 13 to 15 are illustrative of a further embodiment of the present invention where like numbers have been added to like members to illustrate the similarities between the respective embodiments. In this embodiment, the tubular member 32 is substantially similar to the tubular member 32 described above and shown in FIGS. 10–12. The tubular member 32 includes one or more side openings or ports 64 along the proximal end thereof and a hemostatic valve 65 at the proximal end thereof. As shown in FIG. 13, the anchor member 30 is initially deployed in the manner described above with respect to the prior embodiment and shown in FIGS. 1–7. The side port 64 of the tubular body 32 is in flow communication with an outlet 66 which is located on the interior of the tubular body 32 as shown in FIG. 13. Next, the plunger member 38 is retracted and withdrawn from the tubular member 32. The user then connects the syringe assembly 33 to the side port 64 in the manner shown in FIG. 14 while the hemostatic valve 65 seals the proximal end of the tubular body 32. If conventional single chamber syringes are to be used, it may be desirable to use multiple side ports such that the thrombin and fibrinogen materials, 54 and 56, are not mixed until they are injected into the incision 28. In the embodiment shown, the dual chamber syringe assembly 33 includes the reconstituted thrombin and fibrin materials, 54 and 56, therein. Once the syringe assembly 33 is connected to the side port, the fibrin and thrombin materials may be ejected from the syringe assembly 33 and into the interior of the tubular body 32. The user may allow then allow the gelatinous material 52 to cure for a short period of time in the tubular body 32 so that the gelatinous material 52 frictionally engages the filament member 36. Once the gelatinous material 52 has begun to cure, the tubular body 32 may be withdrawn from the incision so that the gelatinous material 52 is positioned in the incision in engagement with the filament member 36 and adjacent to the anchor member 30.

Figure 16:
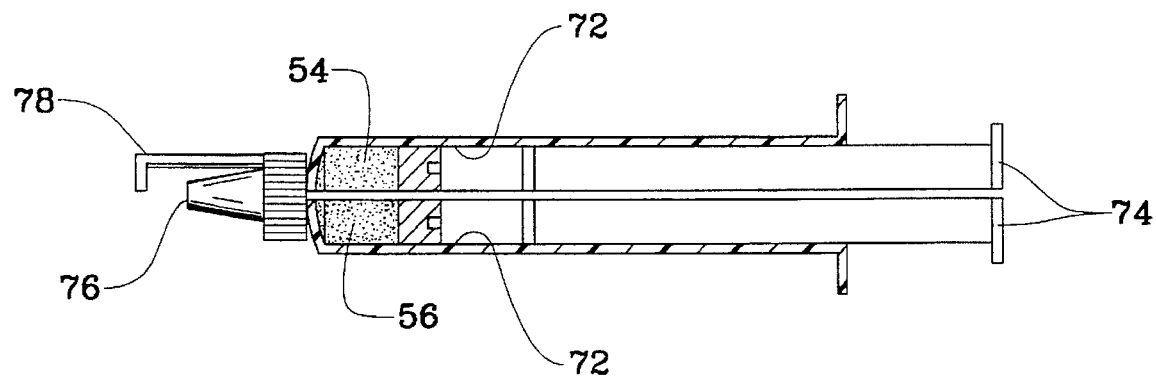
FIG. 16 is a side view, partially in cross section, showing the syringe assembly of an alternate embodiment of the present invention.
Figure 17:
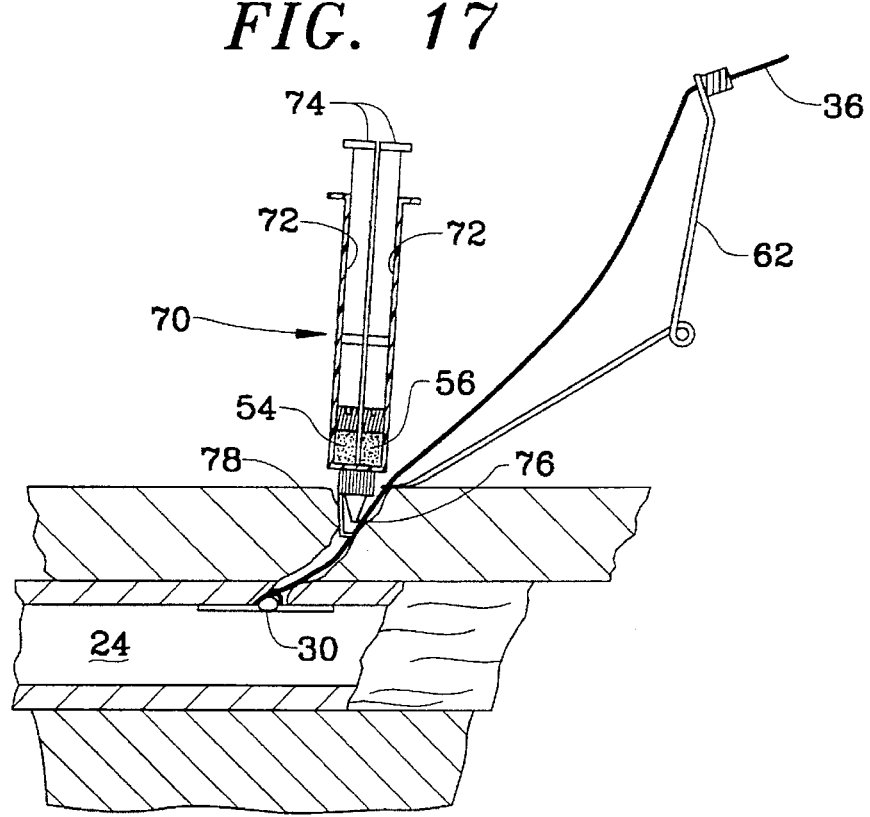
FIG. 17 is a side view, partially in cross section, showing the syringe assembly of the embodiment shown in FIG. 16 positioned in the puncture along the filament member.
Figure 18:
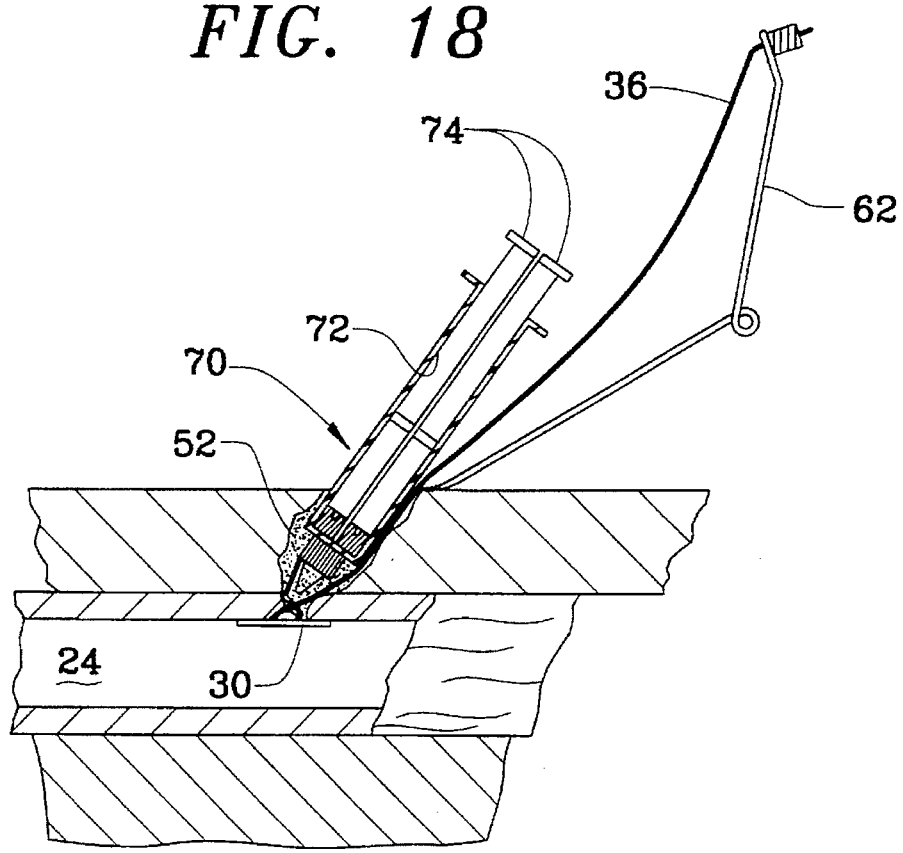
FIG. 18 is a side view, partially in cross section, showing the syringe assembly of the embodiment shown in FIG. 16 with the gelatinous material injected into the incision.

FIGS. 16 to 18 illustrate a further embodiment of the present invention where like numbers have been added to like members to illustrate the similarities between the respective embodiments. In this embodiment, the anchor member 30 is positioned along the wall of the artery in the manner described above and shown in FIGS. 1–7. The sheath 26 and the tubular body 32 are then removed from the puncture to leave only the anchor member 30 and filament member 36 in the incision and blood vessel. A spring member 62, similar to the spring member described above, may then be placed on the filament member 36 to retain the anchor member along the wall of the blood vessel and maintain a slight and continuous pressure on the anchor member 30. Next a modified syringe assembly 70 (FIG. 16) may be attached to the filament member 36 in the manner shown in FIG. 17. The syringe assembly 70 of this embodiment preferably includes two separate chambers 72 and plunger members 74 therein and a common outlet 76. The distal end of the syringe assembly 70 is preferably tapered slightly and includes a generally U-shaped clip member 78 thereon. The clip member 78 is designed to slidably engage or clip onto the filament member 36 so that the syringe assembly 70 is movable distally along the filament member 36 in the incision to the position shown in FIG. 18 wherein the clip member 78 contacts the anchor member 30. The use of the clip member on the distal end of the syringe assembly 70 ensures the proper alignment between the outlet 76 of the syringe assembly 70 and the filament member 36 so that as the gelatinous material 52 is injected into the puncture, the gelatinous material surrounds the filament member 36. Therefore, the frictional engagement between the gelatinous material 52 and the filament member 36 will be assured as the gelatinous material cures. Additionally, as shown in FIG. 18, the outlet of the syringe assembly 70 is spaced apart a fixed distance from the clip member 78 so that as the syringe assembly 70 is moved along the filament member 36, the clip member 78 will contact the anchor member 30 to stop further distal movement of the syringe assembly 70. Once the clip member 78 reaches the anchor member 30, the outlet 76 will be spaced apart the desired distance from the anchor member 30 and the gelatinous material 52 may be ejected from the syringe assembly 70 without injecting the gelatinous material 52 into the blood vessel of the patient.

Figure 21:
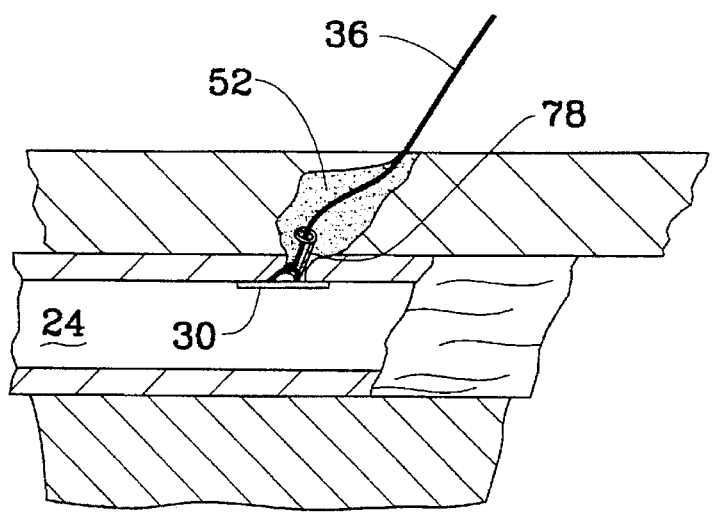
FIG. 21 is a side view, partially in cross section, showing the gelatinous material, clip member and anchor member of the embodiment shown in FIG. 19 in the incision in the body of the patient.
Figure 19:
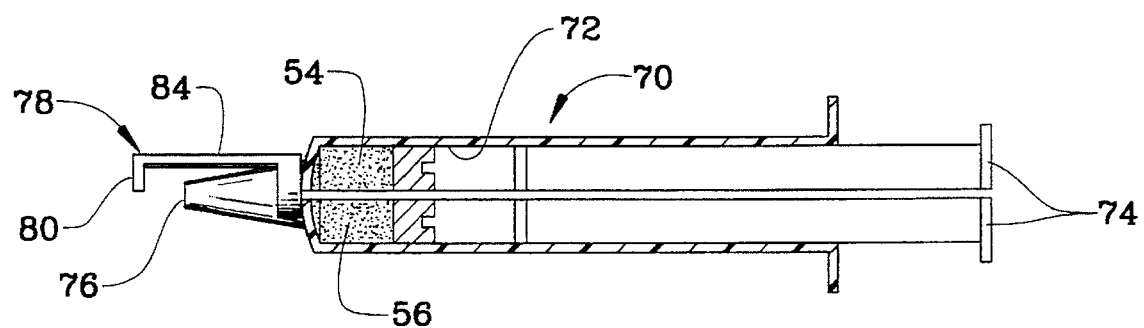
FIG. 19 is a side view, partially in cross section, showing an alternate embodiment of the syringe assembly similar to the embodiment shown in FIG. 16.
Figure 20:
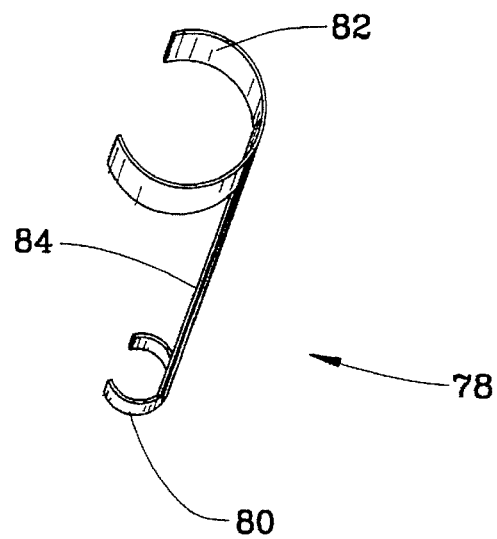
FIG. 20 is an elevated perspective view, showing the clip member of the embodiment shown in FIG. 19.

An alternate form of the clip member and syringe assembly described above and shown in FIGS. 16 to 18 is shown in FIGS. 19 to 21. As best shown in FIG. 20, the clip member 78 is preferably formed as a member which is separate from the syringe assembly 70. In this alternate embodiment, the clip member 78 includes a relatively small semicircularly shaped distal end 80 and a larger semicircularly shaped proximal end 82 which is sized to temporarily engage the distal end of the syringe assembly 70. The distal and proximal ends, 80 and 82, are interconnected by a generally elongate body member 84. It is contemplated that the clip member 78 of this alternate embodiment may be formed of a bioabsorbable material so that the gelatinous material 52 may be injected in the incision and allowed to cure around the clip member 78. Therefore, once the gelatinous material 52 initially cures, the syringe assembly 70 may be removed while the clip member 78 remains in the incision. This embodiment may be further modified such that the distal end 80 of the clip member 78 physically engages the head member 68 of the anchor member 30 such as with a snap fit or other type of locking arrangement. Therefore, in this embodiment, as the syringe assembly 70 is removed from the incision, the clip member 78 is released from the distal end of the syringe assembly 70 and remains in the incision in engagement with the anchor member 30. The syringe assembly 70 of this embodiment functions as a positioning member to position the clip member 78 in the incision, and the clip member 78 of this embodiment functions as a spacer to ensure that the distal end of the syringe assembly 70 is spaced apart from the anchor member 30. The clip member 78 of this alternate embodiment is particularly useful in situations where it is desirable to use radiopaque materials to identify the location of the incision for future resticks. For example, it is contemplated that the clip member 78 may be formed of a bioabsorbable material similar to that of the anchor member 30 and at least the body member 84 thereof may readily include a radiopaque material formulated therein. The use of the radiopaque material in the clip member 78 is particularly attractive because the clip member 78 is positioned at the opening in the wall of the blood vessel and this is an area of concern to the physician when the physician is interested in performing resticks or further procedures. Yet another advantage of the detachable type of clip member 78 relates to the respective sizes of the distal end 80 and proximal end 82 of the clip member 78. Because the proximal end 82 of the clip member 78 is preferably larger than the distal end 80 of the clip member 78, the tissue will constrict in an hour glass shape along the length of the clip member 78 to further assist in retaining the anchor member 30, clip member 78 and gelatinous material 52 in the desired position in the incision as generally shown in FIG. 21 as the gelatinous material 52 cures.

As should be appreciated from the foregoing, the syringe assemblies and introducing assemblies of the subject invention and their method of use enables the ready, effective and efficient sealing of an opening, such as a puncture or incision in body organs, cavities or tissue, be it a blood vessel, a lumen, a duct, or other opening formed in the body of the patient. For example, the sealing assembly and its method of use can be used for the purpose of sealing percutaneous transhepatic punctures to preclude the risk of bile leakage into the peritoneum, via the liver puncture site after arthroscopic or laparoscopic procedures or even along the spinal column after spinal punctures. Moreover, the closures, instruments and their method of use may also be used for sealing percutaneous incisions in the lung or heart which may occur from a wound or other trauma.

What is claimed is:

1. An assembly for sealing an incision in the body of a patient wherein the incision extends from the skin of the patient into a blood vessel, duct, lumen or body cavity of the patient, the assembly comprising;

a first member formed of a bioabsorbable material and sized to be positioned in the blood vessel, duct or lumen of the patient;

a second member formed of a bioabsorbable and injectable liquid hemostasis promoting material and said second member is formed to cooperatively seal the incision from the flow of fluids therethrough in combination with said first member; and a third member extending proximally from said first member and having greater flexibility than said first member.

2. The assembly of claim 1 wherein said second member is formed of an injectable hemostasis promoting material which is injectable along said third member and is absorbable within the body of the patient.

3. The assembly of claim 1 further including said third member extending from said first member and through at least a portion of said second member.

4. The assembly of claim 1 wherein said third member is a filament member and said third member is frictionally engaged with at least one of said first member or said second member.

5. The assembly of claim 1 wherein said third member is a flexible filament member which extends substantially through said second member.

6. The assembly of claim 1 wherein said third member is at least partially encircled by said second member.

7. The assembly of claim 1 wherein said first member is an anchor member.

8. The assembly of claim 1 wherein said second member is formed of a tissue glue which is injected into the incision in the body of the patient.

9. The assembly of claim 1 wherein said first member is sized to be operatively positionable in the blood vessel of a patient and said second member is operatively positionable in the incision in use and said third member extends between said first member and said second member such that said first member, said second member and said third member cooperatively seal the incision to obstruct the flow of blood from the blood vessel through the incision.

10. An assembly for sealing an incision in the body of a patient wherein the incision extends from the skin of the patient into a blood vessel, duct, lumen or body cavity of the patient, the assembly comprising;

a first member formed of a bioabsorbable material and sized to be positioned in the blood vessel, duct or lumen of the patient;

a second member formed of a bioabsorbable and gelatinous hemostasis promoting material and said second member is formed to cooperatively seal the incision from the flow of fluids therethrough in combination with said first member;

a third member extending proximally from said first member and having greater flexibility than said first member; and said second member is formed of a plurality of injectable materials which are mixed together to coagulate in the incision and seal the incision from the flow of fluids therethrough.

11. The assembly of claim 10 wherein said materials include a thrombin containing material therein.

12. The assembly of claim 10 wherein said materials include a fibrinogen containing material therein.

13. An assembly for sealing an incision in the body of a patient wherein the incision extends from the skin of the patient into a blood vessel, duct or lumen of the patient, the assembly comprising;

a first member formed of a bioabsorbable material and sized to be positionable in the blood vessel, duct, body cavity or lumen of the patient;

a second member formed of a bioabsorbable and injectable liquid hemostasis promoting material and said second member is formed to cooperatively seal the incision from the flow of fluids therethrough in combination with said first member;

an insertion assembly including an elongate tubular member to facilitate the insertion of at least one of said first member or said second member into the incision; and a third member sized to extend proximally from the first member and along the lengthwise dimension of the incision and said third member having greater flexibility than said first member.

14. The assembly of claim 13 wherein said tubular member is an elongate introducer member and said first member is expelled therefrom into the blood vessel, duct or lumen of the patient.

15. The assembly of claim 13 wherein said tubular member includes a means for ejection associated therewith and said second member is ejected therefrom.

16. The assembly of claim 13 wherein said tubular member includes an injection port thereon and said second member is injected therethrough.

17. An assembly for sealing an incision in the body of a patient wherein the incision extends from the skin of the patient into a blood vessel, duct or lumen of the patient, the assembly comprising;

a first member formed of a bioabsorbable material and sized to be positionable in the blood vessel, duct, body cavity or lumen of the patient;

a second member formed of a bioabsorbable and gelatinous hemostasis promoting material and said second member for cooperatively sealing the incision from the flow of fluids therethrough in combination with said first member;

an insertion assembly including an elongate tubular member to facilitate the insertion of at least one of said first member or said second member into the incision; and a syringe assembly having a plurality of chambers therein and said chambers include at least a portion of said second member therein.

18. A method of sealing an incision formed in the body of a patient wherein the incision extends generally from the skin of a patient into a selected blood vessel of the patient, the method comprising;

inserting a first member through the incision to a location generally adjacent to the wall of the blood vessel and causing a third member which is more flexible than the first member to extend proximally from the first member into the incision; and then injecting a gelatinous hemostasis promoting material into the incision such that the gelatinous material is positioned in the incision proximally of the first member and generally adjacent to the third member to seal the incision from the flow of blood passing through the blood vessel.

19. The method of claim 18 further including the step of ejecting the gelatinous material which includes a tissue glue from a syringe member into the incision.

20. The method of claim 18 further including the step of injecting a plurality of materials including thrombin and fibrinogen into the incision to form the gelatinous material.

21. The method of claim 18 further including the step of inserting the third member which is a filament member into the incision so that the filament member is frictionally engaged by the gelatinous material in the incision as the gelatinous material cures in the incision to cause the first member to be retained in the desired location generally adjacent to the wall of the blood vessel.

22. The method of claim 18 including the step of injecting the gelatinous material into the incision through a syringe.

23. The method of claim 22 further including the step of injecting the gelatinous material into the incision and along a filament member which is operatively connected to the first member.

24. The method of claim 23 further including the step of injecting the gelatinous material into the incision through the syringe which is movable into the incision along the filament member so that the gelatinous material cures in the incision to seal the incision from the flow of fluids therethrough.

25. The method of claim 18 further including the step of injecting a material containing thrombin therein as part of the gelatinous material in the incision through a syringe assembly which is inserted into the incision.

26. The method of claim 18 further including the step of injecting a material containing fibrin therein as part of the gelatinous material in the incision through a syringe assembly which is inserted into the incision.

27. The method of claim 18 further including the step of injecting separate materials containing thrombin and fibrin therein through a syringe assembly which is inserted into the incision and mixing the fibrin and thrombin in the incision to form the gelatinous material in the incision.

28. A method of sealing an incision formed in the body of a patient wherein the incision extends generally from the skin of a patient into a selected blood vessel of the patient, the method comprising;

inserting a first member into the incision to a location generally adjacent to the wall of the blood vessel; and injecting a gelatinous material into the incision using a syringe assembly such that the gelatinous material is positioned in the incision proximally of the first member to seal the incision from the flow of blood passing through the blood vessel by inserting the syringe assembly into the incision along a filament member to insert the distal end portion of the syringe assembly into the incision at a desired location and then ejecting the gelatinous material therefrom.

* * * * *